United States Patent
Mukhopadhyay et al.

(10) Patent No.: US 11,304,916 B2
(45) Date of Patent: Apr. 19, 2022

(54) METHODS AND COMPOSITIONS FOR THE TREATMENT OF SHIGA TOXICOSIS

(71) Applicant: Board of Regents, The University of Texas System, Austin, TX (US)

(72) Inventors: Somshuvra Mukhopadhyay, Austin, TX (US); Andrey S. Selyunin, Kyle, TX (US); Stanton F. McHardy, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 16 days.

(21) Appl. No.: 16/890,710

(22) Filed: Jun. 2, 2020

(65) Prior Publication Data

US 2020/0375923 A1 Dec. 3, 2020

Related U.S. Application Data

(60) Provisional application No. 62/856,561, filed on Jun. 3, 2019.

(51) Int. Cl.
| | |
|---|---|
| *A61K 31/138* | (2006.01) |
| *A61K 33/32* | (2006.01) |
| *A61P 31/04* | (2006.01) |
| *A61K 31/4535* | (2006.01) |
| *A61K 9/00* | (2006.01) |
| *A61K 45/06* | (2006.01) |

(52) U.S. Cl.
CPC ........ *A61K 31/138* (2013.01); *A61K 31/4535* (2013.01); *A61K 33/32* (2013.01); *A61P 31/04* (2018.01); *A61K 9/0053* (2013.01); *A61K 45/06* (2013.01)

(58) Field of Classification Search
CPC .................................................. A61K 31/138
See application file for complete search history.

(56) References Cited

PUBLICATIONS

Selyunin, A.S., et al. "Tamoxifen blocks retrograde trafficking of Shiga toxin 1 and 2 and protects against lethal toxicosis." Life Science Alliance. (2019), vol. 2, No. 3, pp. 1-14 of 14. (Year: 2019).*
Mukhopadhyay, S. & Linstedt, A.D. (2012), "Manganese Blocks Intracellular Trafficking of Shiga Toxin and Protects Against Shiga Toxicosis"., Science 335, (6066):332-335.*
Mukhopadhyay, S., Redler B., & Linstedt A.D., (2013) "Shiga Toxin-Binding Site for Host Cell Receptor, GPP130 Reveals Unexpected Divergence in Toxin-Trafficking Mechanisms"., Mol. Biol. Cell., 24(15):2311-2318.*
Selyunin, A.S., Iles, L.R., Bartholomeusz, G., & Mukhopadhyay, S. (2017), "Genome-Wide SIRNA Screen Identifies UNC50 as a Regulator of Shiga Toxin 2 Trafficking"., J. Cell Biol. 216(10):3249-3262.*

Selyunin, A.S. & Mukhopadhyay, S. (2015) "A Conserved Structural Motif Mediates Retrograde Trafficking of Shiga Toxin Types 1 and 2"., Traffic 16(12):1270-1287.*
Saenz, J.B., Doggett, T.A., & Haslam, D.B., (2007) "Identification and Characterization of Small Molecules that Inhibit Intracellular Toxin Transport"., Infect. Immun., 75(9):4552-4561.*
Mukhopadhyay, S. & Linstedt, A.D., (2013) "Retrograde Trafficking of AB(5) Toxins Mechanisms to Therapeutics". J. Mol. Med. (Berl), 91 (10):1131-1141.
Stechmann, B. et al. (2010) "Inhibition of Retrograde Transport Protects Mice from Lethal Ricin Challenge"., Cell 141(2):231-242.
Wartosch, L., Gunesdogan, U., Graham,S.C., & Luzio, J.P., (2015) "Recruitment of VPS33A to HOPS by VPS16 Is Required for Lysosome Fusion with Endosomes and Autophagosomes"., Traffic 16(7):727-742.
Pols, M.S., Ten, Brink C., Gosavi, P., Oorschot, V., & Klumperman, J. (2013), "The HOPS Proteins hVps41 and hVps39 are Required for Homotypic and Heterotypic Late Endosome Fusion"., Traffic 14(2):219-232.
Jiang, P., et. al. (2014) "The HOPS Complex Mediates Autophagosome-Lysosome Fusion Through Interaction with Syntaxin 17"., Mol. Biol. Cell 25(8):1327-1337.
Huotari, J. & Helenius, A., (2011) "Endosome Maturation"., EMBO, J., 30(17):3481-3500.
Van Weert, A.W., Dunn, K.W., Geuze, H.J., Maxfield, F.R., & Stoorvogel, W., (1995) "Transport From Late Endosomes to Lysosomes, But Not Sorting of Integral Membrane Proteins in Endosomes, Depends on the Vacuolar Proton Pump"., J. Cell. Biol. 130(4):821-834.
Chapman, R.E., & Munro, S., (1994) "Retrieval of TGN Proteins From the Cell Surface Requires Endosomal Acidification"., EMBO, J., 13(10):2305-2312.
Dyve, Lingelem A.B., Bergan, J., & Sandvig, K., (2012) "Inhibitors of Intravesicular Acidification Protect against Shiga Toxin in a pH-Independent Manner"., Traffic 13(3):443-454.
Altan, N., Chen, Y., Schindler, M., & Simon, S.M., (1999) "Tamoxifen Inhibits Acidification in Cells Independent of the Estrogen Receptor"., Proc. Natl. Acad. Sci. U.S.A., 96(8):4432-4437.
Chen, Y., Schindler, M., & Simon, S.M., (1999) "A Mechanism for Tamoxifen-Mediated Inhibition of Acidification"., J. Biol. Chem. 274(26):18364-18373.
Lu,S., Sung,T., Lin, N., Abraham, R.T., & Jessen, B.A., (2017) "Lysosomal Adaptation: How Cells Respond to Lysosomotropic Compounds"., PLoS One 12(3):e0173771.

(Continued)

*Primary Examiner* — John S Kenyon
(74) *Attorney, Agent, or Firm* — Kilpatrick, Townsend & Stockton, LLP

(57) ABSTRACT

Methods for treating Shiga toxicosis, caused by infection with Shiga toxin bacteria, are provided. The methods include administering to a subject in need thereof an effective amount of one or more active agents selected from tamoxifen, 4-hydroxytamoxifen, endoxifen, toremifene, raloxifene, bazedoxifene, and pharmaceutically acceptable salts thereof. In some embodiments, the methods further include the administration of an antibiotic or a manganese compound to the subject. Pharmaceutical compositions for the treatment of Shiga toxicosis are also described.

12 Claims, 25 Drawing Sheets
Specification includes a Sequence Listing.

(56) References Cited

PUBLICATIONS

Lazzeroni, M., et al. (2012) "Oral Low Dose and Topical Tamoxifen for Breast Cancer Prevention: Modern Approaches for an Old Drug"., Breast Cancer Res. 14(5):214.

Robinson, S.P., Langan-Fahey, S.M., Johnson, D.A., & Jordan, V.C., (1991) "Metabolites, Pharmacodynamics, and Pharmacokinetics of Tamoxifen in Rats and Mice Compared to the Breast Cancer Patient"., Drug Metab. Dispos. 19(1):36-43.

Tisdale, E.J., (2000) "Rab2 Requires PKC Lota/Lambda to Recruit Beta-COP for Vesicle Formation"., Traffic 1(9):702-712.

Tisdale, E.J. & Balch, W.E., (1996) "Rab2 is Essential for the Maturation of Pre-Golgi Intermediates"., J. Biol. Chem. 271(46):29372-29379.

Tisdale, E.J., Bourne, J.R., Khosravi-Far, R., Der, C.J., & Balch, W.E., (1992) "GTP-Binding Mutants of Rabi and Rab2 are Potent Inhibitors of Vesicular Transport From the Endoplasmic Reticulum to the Golgi Complex"., J. Cell. Biol. 119(4):749-761.

Tisdale, E.J. & Jackson, M.R., (1998) "Rab2 Protein Enhances Coatomer Recruitment to Pre-Golgi Intermediates",. J. Bio.I Chem. 273(27):17269-17277.

Fujita, N., et. al., (2017) "Genetic Screen in *Drosophila* Muscle Identifies Autophagy-Mediated T-Tubule Remodeling and a Rab2 Role in Autophagy"., Elife 6.

Gillingham, A.K., Sinka, R., Torres, I.L., Lilley, K.S., & Munro, S., (2014) "Toward a Comprehensive Map of the Effectors of Rab GTPases"., Dev. Cell. 31(3):358-373.

Lorincz, P., et. al., (2017) "Rab2 Promotes Autophagic and Endocytic Lysosomal Degradation"., J. Cell. Biol. 216(7):1937-1947.

Bache, K.G., Raiborg, C., Mehlum, A., & Stenmark, H., (2003) "STAM and Hrs are Subunits of a Multivalent Ubiquitin-Binding Complex on Early Endosomes"., J. Biol. Chem. 278(14):12513-12521.

Lloyd, T.E., et. al., (2002) "Hrs Regulates Endosome Membrane Invagination and Tyrosine Kinase Receptor Signaling in *Drosophila*"., Cell. 108(2):261-269.

Ren, X., et. al., (2009) "Hybrid Structural Model of the Complete Human ESCRT-0 Complex",. Structure 17(3):406-416.

Rusten, T.E., & Stenmark, H., (2009) "How Do ESCRT Proteins Control Autophagy?"., J. Cell. Sci. 122(Pt 13):2179-2183.

Tan, K.P., et. al., (2016) "Fucosylation of LAMP-1 and LAMP-2 by FUT1 Correlates with Lysosomal Positioning and Autophagic Flux of Breast Cancer Cells"., Cell Death Dis. 7(8):e2347.

Danyang, Li, et.al., "Targeting the Early Endosome-to-Golgi Transport of Shiga Toxins as a Therapeutic Strategy", Division of Pharmacology & Toxicology, et al., 15 pgs.

\* cited by examiner

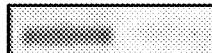
```
             312                              332
WT     ...MGPRMVNLSE CMDPKRLAESS...
           **********
ΔATG7  [...MGPRMVNLSE LYGPStop...
        ...MGPRMVNLSE LYGPSKVSStop...
```
FIG. 2A
```
             140                                              178
WT     ...AFHTTEAEAS SQSLTQIYALPEIPQDQNAAESWETLEAD...
          ********** ****
ΔSTX17 [...AFHTTEAEAS SQSLKRTStop
        ...AFHTTEAEAS SQSLTQIYALPEIPQDQNAADRGKPStop
```
FIG. 2B
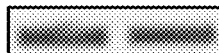
FIG. 2C
FIG. 2D

3° amine

Toremifene (TOR)    Bazedoxifene (BAZ)

SEQUENCE LISTING

```
<160> NUMBER OF SEQ ID NOS: 32

<210> SEQ ID NO 1
<211> LENGTH: 26
<212> TYPE: PRT
<213> ORGANISM: Artificial Sequence
<220> FEATURE:
<223> OTHER INFORMATION: Synthetic construct

<400> SEQUENCE: 1

Gln Phe Thr Asp Lys Arg Phe Gln Pro Val His Asp Leu Thr Ile Gly
1               5                   10                  15

Val Glu Phe Gly Ala Arg Met Ile Thr Ile
            20                  25

<210> SEQ ID NO 2
<211> LENGTH: 14
<212> TYPE: PRT
<213> ORGANISM: Artificial Sequence
<220> FEATURE:
<223> OTHER INFORMATION: Synthetic construct

<400> SEQUENCE: 2

Gln Phe Thr Asp Lys Arg Phe Gln Pro Val His Asp Leu Val
1               5                   10

<210> SEQ ID NO 3
<211> LENGTH: 21
<212> TYPE: PRT
<213> ORGANISM: Artificial Sequence
<220> FEATURE:
<223> OTHER INFORMATION: Synthetic construct

<400> SEQUENCE: 3

Met Gly Pro Arg Met Val Asn Leu Ser Glu Cys Met Asp Pro Lys Arg
```

```
1               5                   10                  15

Leu Ala Glu Ser Ser
            20

<210> SEQ ID NO 4
<211> LENGTH: 14
<212> TYPE: PRT
<213> ORGANISM: Artificial Sequence
<220> FEATURE:
<223> OTHER INFORMATION: Synthetic construct

<400> SEQUENCE: 4

Met Gly Pro Arg Met Val Asn Leu Ser Glu Leu Tyr Gly Pro
1               5                   10

<210> SEQ ID NO 5
<211> LENGTH: 18
<212> TYPE: PRT
<213> ORGANISM: Artificial Sequence
<220> FEATURE:
<223> OTHER INFORMATION: Synthetic construct

<400> SEQUENCE: 5

Met Gly Pro Arg Met Val Asn Leu Ser Glu Leu Tyr Gly Pro Ser Lys
1               5                   10                  15

Val Ser

<210> SEQ ID NO 6
<211> LENGTH: 39
<212> TYPE: PRT
<213> ORGANISM: Artificial Sequence
<220> FEATURE:
<223> OTHER INFORMATION: Synthetic construct

<400> SEQUENCE: 6

Ala Phe His Thr Thr Glu Ala Glu Ala Ser Ser Gln Ser Leu Thr Gln
1               5                   10                  15

Ile Tyr Ala Leu Pro Glu Ile Pro Gln Asp Gln Asn Ala Ala Glu Ser
            20                  25                  30

Trp Glu Thr Leu Glu Ala Asp
        35

<210> SEQ ID NO 7
<211> LENGTH: 17
<212> TYPE: PRT
<213> ORGANISM: Artificial Sequence
<220> FEATURE:
<223> OTHER INFORMATION: Synthetic construct

<400> SEQUENCE: 7

Ala Phe His Thr Thr Glu Ala Glu Ala Ser Ser Gln Ser Lys Leu Arg
1               5                   10                  15

Thr

<210> SEQ ID NO 8
<211> LENGTH: 35
<212> TYPE: PRT
<213> ORGANISM: Artificial Sequence
<220> FEATURE:
<223> OTHER INFORMATION: Synthetic construct

<400> SEQUENCE: 8

Ala Phe His Thr Thr Glu Ala Glu Ala Ser Ser Gln Ser Leu Thr Gln
1               5                   10                  15
```

Ile Tyr Ala Leu Pro Glu Ile Pro Gln Asp Gln Asn Ala Ala Asp Arg
            20                  25                  30

Gly Lys Pro
        35

<210> SEQ ID NO 9
<211> LENGTH: 20
<212> TYPE: DNA
<213> ORGANISM: Artificial Sequence
<220> FEATURE:
<223> OTHER INFORMATION: Synthetic construct

<400> SEQUENCE: 9
ccagtgcatg accttactat                                                 20

<210> SEQ ID NO 10
<211> LENGTH: 20
<212> TYPE: DNA
<213> ORGANISM: Artificial Sequence
<220> FEATURE:
<223> OTHER INFORMATION: Synthetic construct

<400> SEQUENCE: 10
ggtgaacctc agtgaatgta                                                 20

<210> SEQ ID NO 11
<211> LENGTH: 20
<212> TYPE: DNA
<213> ORGANISM: Artificial Sequence
<220> FEATURE:
<223> OTHER INFORMATION: Synthetic construct

<400> SEQUENCE: 11
atcaaaatgc tgcagaatcg                                                 20

<210> SEQ ID NO 12
<211> LENGTH: 18
<212> TYPE: DNA
<213> ORGANISM: Artificial Sequence
<220> FEATURE:
<223> OTHER INFORMATION: Synthetic construct

<400> SEQUENCE: 12
caaccatata taatcgct                                                   18

<210> SEQ ID NO 13
<211> LENGTH: 21
<212> TYPE: DNA
<213> ORGANISM: Artificial Sequence
<220> FEATURE:
<223> OTHER INFORMATION: Synthetic construct

<400> SEQUENCE: 13
gccucccuac aucauugcat t                                               21

<210> SEQ ID NO 14
<211> LENGTH: 21
<212> TYPE: DNA
<213> ORGANISM: Artificial Sequence
<220> FEATURE:
<223> OTHER INFORMATION: Synthetic construct

<400> SEQUENCE: 14
ugcaaugaug uagggaggct g                                               21

```
<210> SEQ ID NO 15
<211> LENGTH: 21
<212> TYPE: DNA
<213> ORGANISM: Artificial Sequence
<220> FEATURE:
<223> OTHER INFORMATION: Synthetic construct

<400> SEQUENCE: 15
gccagaggau ucaacaugat t                                              21

<210> SEQ ID NO 16
<211> LENGTH: 21
<212> TYPE: DNA
<213> ORGANISM: Artificial Sequence
<220> FEATURE:
<223> OTHER INFORMATION: Synthetic construct

<400> SEQUENCE: 16
ucauguugaa uccucuggct t                                              21

<210> SEQ ID NO 17
<211> LENGTH: 25
<212> TYPE: RNA
<213> ORGANISM: Artificial Sequence
<220> FEATURE:
<223> OTHER INFORMATION: Synthetic construct

<400> SEQUENCE: 17
ggaaaccuua gaagcggacu uaauu                                          25

<210> SEQ ID NO 18
<211> LENGTH: 25
<212> TYPE: RNA
<213> ORGANISM: Artificial Sequence
<220> FEATURE:
<223> OTHER INFORMATION: Synthetic construct

<400> SEQUENCE: 18
aauuaagucc gcuucuaagg uuucc                                          25

<210> SEQ ID NO 19
<211> LENGTH: 24
<212> TYPE: DNA
<213> ORGANISM: Artificial Sequence
<220> FEATURE:
<223> OTHER INFORMATION: Synthetic construct

<400> SEQUENCE: 19
cagacaagag gtttcagcca gtgc                                           24

<210> SEQ ID NO 20
<211> LENGTH: 24
<212> TYPE: DNA
<213> ORGANISM: Artificial Sequence
<220> FEATURE:
<223> OTHER INFORMATION: Synthetic construct

<400> SEQUENCE: 20
gctcctgctg cacctctgta atac                                           24

<210> SEQ ID NO 21
<211> LENGTH: 22
<212> TYPE: DNA
<213> ORGANISM: Artificial Sequence
<220> FEATURE:
<223> OTHER INFORMATION: Synthetic construct
```

<400> SEQUENCE: 21
gccctgctca cacagtgcaa cc                                        22

<210> SEQ ID NO 22
<211> LENGTH: 24
<212> TYPE: DNA
<213> ORGANISM: Artificial Sequence
<220> FEATURE:
<223> OTHER INFORMATION: Synthetic construct

<400> SEQUENCE: 22
ggcttagcca atgtcccaga gtgg                                      24

<210> SEQ ID NO 23
<211> LENGTH: 21
<212> TYPE: DNA
<213> ORGANISM: Artificial Sequence
<220> FEATURE:
<223> OTHER INFORMATION: Synthetic construct

<400> SEQUENCE: 23
ctctcagcca ggcagtggtc c                                         21

<210> SEQ ID NO 24
<211> LENGTH: 17
<212> TYPE: DNA
<213> ORGANISM: Artificial Sequence
<220> FEATURE:
<223> OTHER INFORMATION: Synthetic construct

<400> SEQUENCE: 24
gcagtagcgg caggagg                                              17

<210> SEQ ID NO 25
<211> LENGTH: 20
<212> TYPE: DNA
<213> ORGANISM: Artificial Sequence
<220> FEATURE:
<223> OTHER INFORMATION: Synthetic construct

<400> SEQUENCE: 25
agtgacgatc ggatgaatga                                           20

<210> SEQ ID NO 26
<211> LENGTH: 18
<212> TYPE: DNA
<213> ORGANISM: Artificial Sequence
<220> FEATURE:
<223> OTHER INFORMATION: Synthetic construct

<400> SEQUENCE: 26
tggtctcatc gctcatgt                                             18

<210> SEQ ID NO 27
<211> LENGTH: 22
<212> TYPE: DNA
<213> ORGANISM: Artificial Sequence
<220> FEATURE:
<223> OTHER INFORMATION: Synthetic construct

<400> SEQUENCE: 27
tcgtgggaaa ccttagaagc gg                                        22

<210> SEQ ID NO 28

```
<211> LENGTH: 22
<212> TYPE: DNA
<213> ORGANISM: Artificial Sequence
<220> FEATURE:
<223> OTHER INFORMATION: Synthetic construct

<400> SEQUENCE: 28
gcagcactgt tgacatggtc tg                                              22

<210> SEQ ID NO 29
<211> LENGTH: 22
<212> TYPE: DNA
<213> ORGANISM: Artificial Sequence
<220> FEATURE:
<223> OTHER INFORMATION: Synthetic construct

<400> SEQUENCE: 29
cctgaactgg acggacatac ca                                              22

<210> SEQ ID NO 30
<211> LENGTH: 22
<212> TYPE: DNA
<213> ORGANISM: Artificial Sequence
<220> FEATURE:
<223> OTHER INFORMATION: Synthetic construct

<400> SEQUENCE: 30
ctttggacca gaagcctcgg tt                                              22

<210> SEQ ID NO 31
<211> LENGTH: 21
<212> TYPE: DNA
<213> ORGANISM: Artificial Sequence
<220> FEATURE:
<223> OTHER INFORMATION: Synthetic construct

<400> SEQUENCE: 31
ggctacactg agcaccaggt g                                               21

<210> SEQ ID NO 32
<211> LENGTH: 17
<212> TYPE: DNA
<213> ORGANISM: Artificial Sequence
<220> FEATURE:
<223> OTHER INFORMATION: Synthetic construct

<400> SEQUENCE: 32
ggtccaccct gttgctg                                                    17
```

US 11,304,916 B2

METHODS AND COMPOSITIONS FOR THE TREATMENT OF SHIGA TOXICOSIS

CROSS-REFERENCE TO RELATED APPLICATION

This application claims priority to U.S. Provisional Patent Application No. 62/856,561, filed on Jun. 3, 2019, entitled "Methods and Compositions for the Treatment of Shiga Toxicosis," the disclosure of which is hereby incorporated by reference in its entirety for all purposes.

STATEMENT AS TO RIGHTS TO INVENTIONS MADE UNDER FEDERALLY SPONSORED RESEARCH AND DEVELOPMENT

This invention was made with government support under Grant No. R21 AI123608 awarded by the National Institutes of Health. The government has certain rights in the invention.

REFERENCE TO A SEQUENCE LISTING SUBMITTED AS A TEXT FILE VIA EFS-WEB

The official copy of the sequence listing is submitted electronically via EFS-Web as an ASCII formatted sequence listing with a file named 093331-1189539_seqlist.txt, created on May 26, 2020, having a size of 7.23 KB, and is filed concurrently with the specification. The sequence listing contained in this ASCII formatted document is part of the specification and is herein incorporated by reference in its entirety.

BACKGROUND OF THE INVENTION

Shiga toxin-producing *E. coli* (STEC) infect over 100,000 individuals each year and are a major cause of lethal food-borne infections (1-3). STEC produce two related toxins, Shiga toxin 1 (STx1) and 2 (STx2), which kill cells by blocking ribosomal protein synthesis (4, 5). Patients infected with STEC initially develop gastrointestinal disease (2, 3). In a subset (~5-15%), the toxins enter the bloodstream and cause life-threatening or fatal renal disease (2, 3). Definitive therapies are not available for STEC infections—there are no antidotes for STx1 and STx2, and antibiotic therapy is generally contraindicated because it may increase toxin release from STEC (2).

STx1 and STx2 are formed by the association of an A subunit, which is catalytically active, with a pentameric B-subunit, which mediates retrograde intracellular trafficking (4-9). Retrograde transport of both toxins involves, sequentially, endocytosis, transit through early endosomes and the Golgi apparatus, and delivery to the endoplasmic reticulum from where the A-subunit is translocated to the cytosol (5-9). Direct transport from early endosomes to the Golgi is critical as it allows the toxins to evade late endosomes where proteolytic enzymes are active (5-9). As STx1 and STx2 must traffic to the cytosol to induce cytotoxicity, blocking toxin transport in general, and at the early endosome-to-Golgi step in particular, has emerged as a promising therapeutic strategy (5, 6, 10, 11). As an example, treatment with manganese degrades the endosomal STx1 receptor GPP130 and thereby blocks the early endosome-to-Golgi transport of STx1, diverts STx1 to late endosomes for degradation, and protects cells and mice against lethal STx1-toxicosis (6). However, in order to be therapeutically effective, a toxin transport inhibitor must block STx2 because STx2 is ~400-times more toxic than STx1 in vivo (12), and in humans, disease severity correlates with STx2 production (13). In spite of the greater disease relevance, molecular mechanisms of STx2 transport, which is GPP130-independent and manganese-insensitive (7), are poorly understood. This gap in knowledge has hindered therapeutic development and, currently, there are no toxin transport inhibitors approved for use in humans.

BRIEF SUMMARY OF THE INVENTION

Provided herein are methods for treating Shiga toxicosis. The methods include administering to a subject in need thereof an effective amount of an active agent selected from the group consisting of tamoxifen, 4-hydroxytamoxifen, endoxifen, toremifene, raloxifene, bazedoxifene, and pharmaceutically acceptable salts thereof. In some embodiments, the subject is infected with a Shiga toxin-producing *Escherichia* species.

In some embodiments, the methods further include the administration of an antibiotic or a manganese compound to the subject. Also provided herein are pharmaceutical compositions containing (i) tamoxifen, 4-hydroxytamoxifen, endoxifen, toremifene, raloxifene, bazedoxifene, or a combination thereof; (ii) a manganese compound, an antibiotic, or a combination thereof; and (iii) one or more pharmaceutically acceptable excipients.

```
                                           (SEQ ID NO: 1)
    (QFTDKRFQPVHDLTIGVEFGARMITI)
    and ΔRab2a (SEQ ID NO: 2)
    (QFTDKRFQPVHDLV).
    HeLa cells
```

Figure 1A:
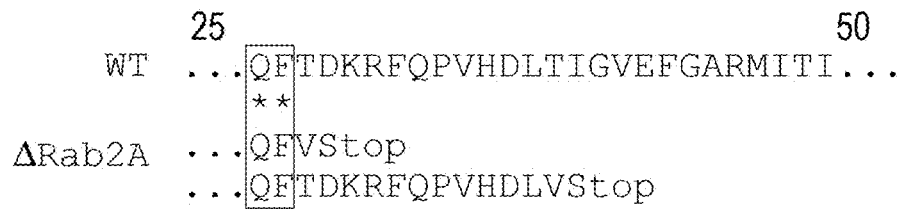
FIG. 1A shows genomic DNA sequences for wild-type
Figure 1B:
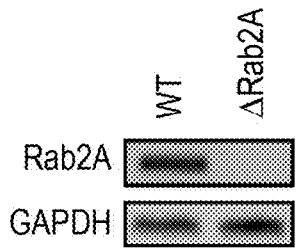

FIG. 1B shows RT-PCR transcripts from wild-type and ΔRab2a HeLa cells.

Figure 1C:
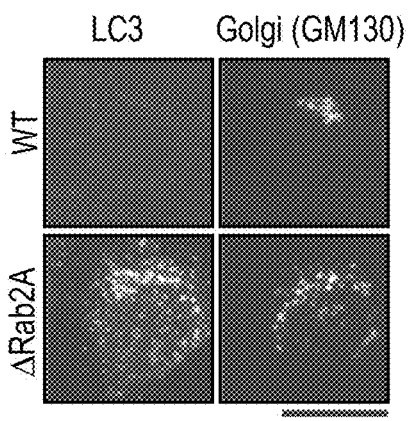

FIG. 1C shows immunofluorescence data collected for wild-type and ΔRab2a HeLa cells. Scale bar, 25 µm.

Figure 1D:
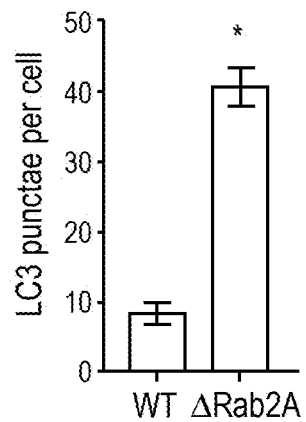

FIG. 1D shows the quantification of LC3 punctae per cell in FIG. 1C. N=15 cells per condition. *p<0.05 by t-test.

Figure 1E:
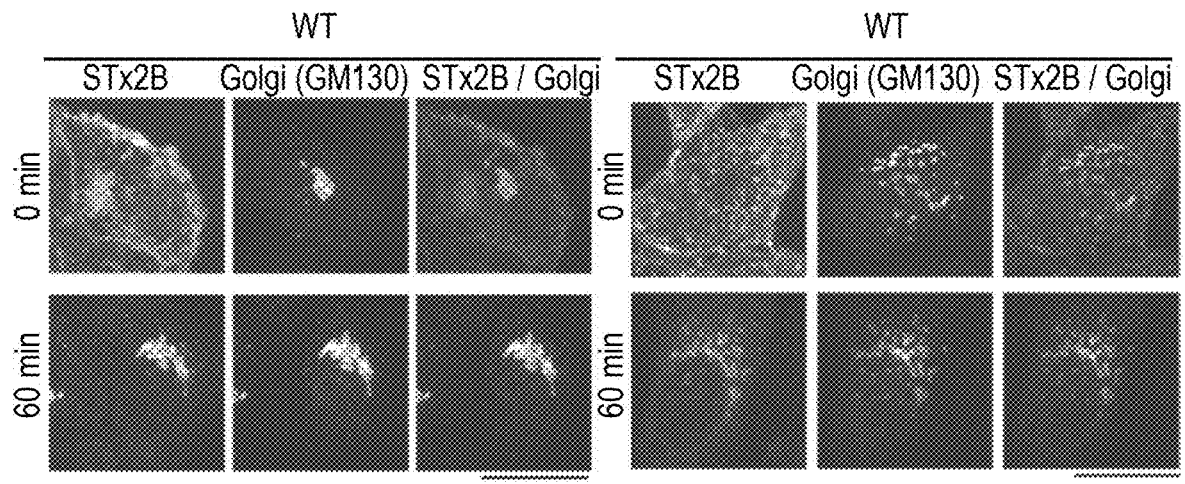

FIG. 1E shows immunofluorescence data collected for wild-type and ΔRab2a HeLa cells, demonstrating STx2B transport. Scale bars, 25 µm.

Figure 1F:
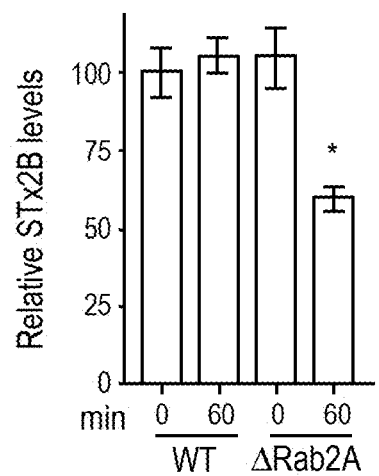

FIG. 1F shows the quantification of relative STx2B levels in FIG. 1E. WT 0 min normalized to 100. N>15 cells per condition. *p<0.05 by one-way ANOVA and Dunnett's post hoc test for comparison between WT at 0 min and other groups.

Figure 1G:
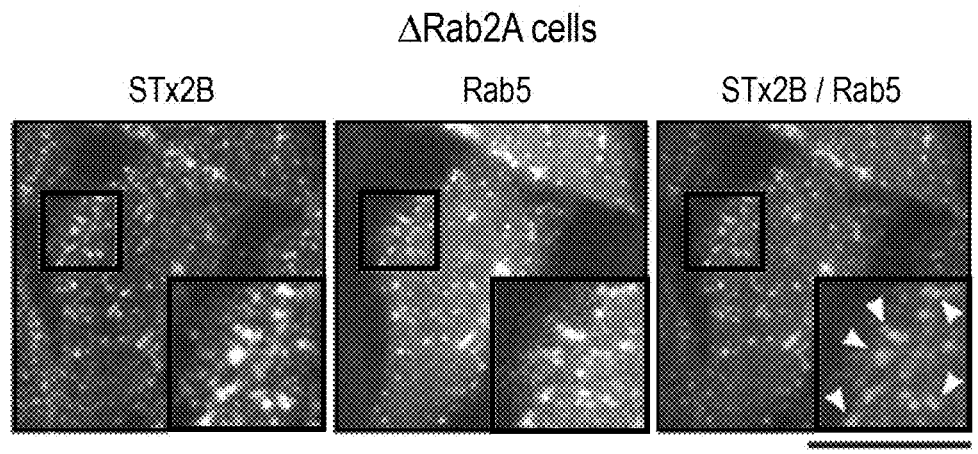

FIG. 1G shows STx2B transport 24 h after transfection with Rab5$_{WT}$. Scale bars, 25 µm.

Figure 1H:
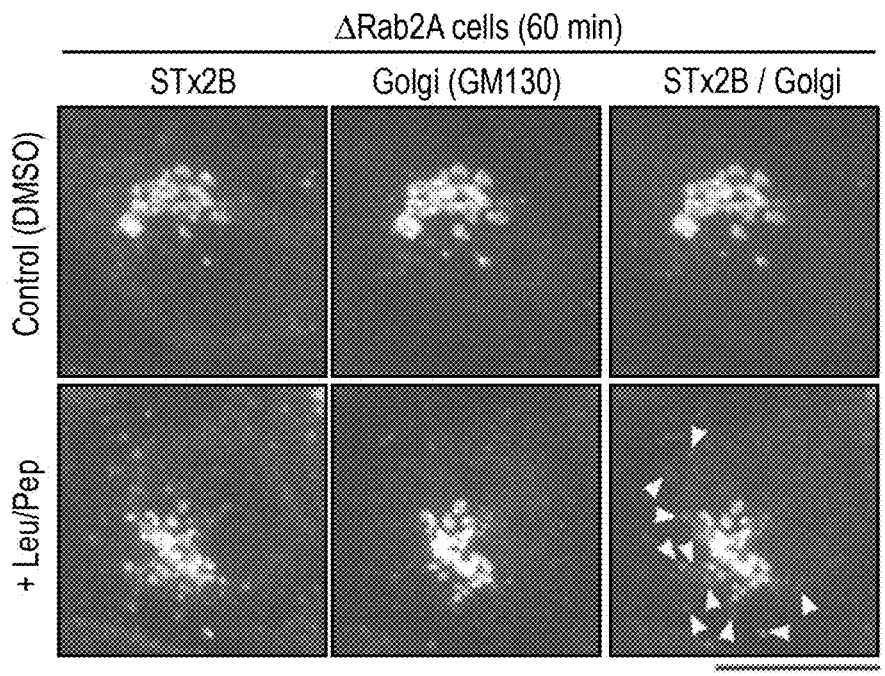

FIG. 1H shows STx2B transport 24 h after exposure to leupeptin (leu) and pepstatin (pep). Scale bars, 25 µm.

Figure 1I:
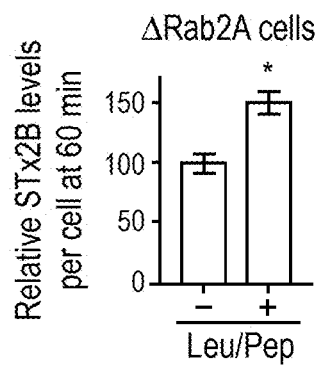

FIG. 1I shows the quantification of relative STx2B levels from FIG. 1H. Levels in untreated cells normalized to 100. N>25 cells per condition. *p<0.05 by t-test.

Figure 1J:
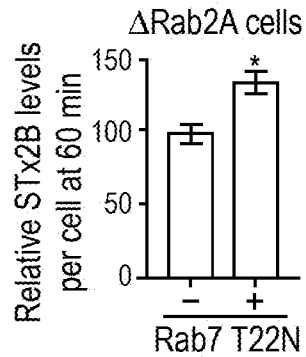

FIG. 1J shows the relative STx2B levels 24 h post-transfection. Levels in untransfected cells normalized to 100. N>15 cells per condition. *p<0.05 by t-test.

Figure 1K:
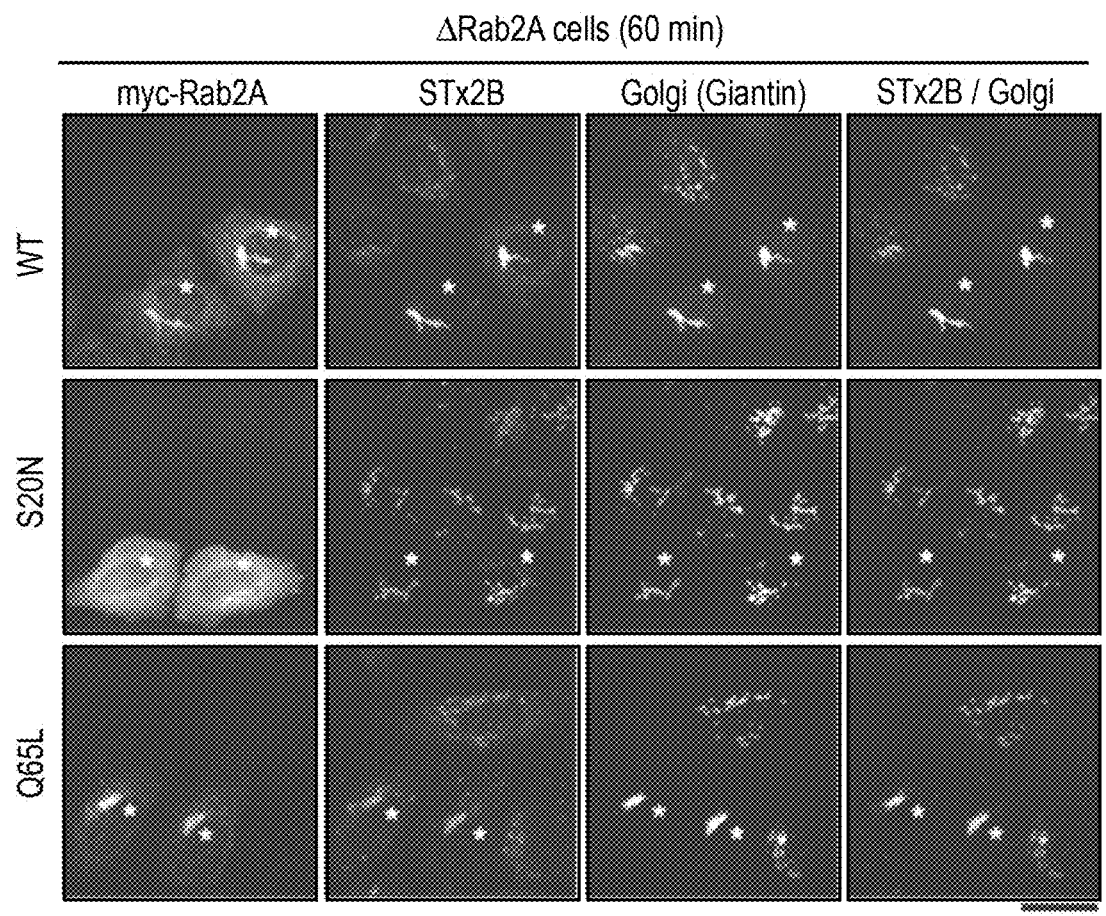

FIG. 1K shows the transport of STx2B 24 h post-transfection. Asterisks—transfected cells. Scale bar, 25 µm.

Figure 1L:
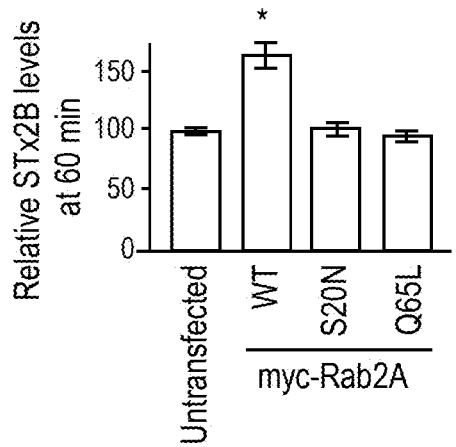

FIG. 1L shows the quantification of relative STx2B levels from FIG. 1K. Values in untransfected cells normalized to 100. N>20 cells per condition. *p<0.05 by one-way ANOVA and Dunnett's post hoc test for comparison between untransfected and other groups. Taken together, FIGS. 1A-1K show that Rab2a is required for the early endosome-to-Golgi transport of STx2B.

FIG. 2A shows genomic DNA sequences for wild-type

```
                                        (SEQ ID NO: 3)
        (MGPRMVNLSECMDPKRLAESS)
        and ΔATG7

(SEQ ID NO: 4)
        (MGPRMVNLSELYGP);

(SEQ ID NO: 5)
        (MGPRMVNLSELYGPSKVS).
        HeLa cells
```

FIG. 2B shows genomic DNA sequences for wild-type

```
                                               (SEQ ID NO: 6)
    (AFHTTEAEASSQSLTQIYALPEIPQDQNAAESWETLEAD)
    and Δsyntaxin17 (ΔSTX17)

(SEQ ID NO: 7)
    (AFHTTEAEASSQSKLRT);

(SEQ ID NO: 8)
    (AFHTTEAEASSQSLTQIYALPEIPQDQNAADRGKP).
    HeLa cells
```

FIG. 2C shows RT-PCR transcripts from wild-type and ΔATG7 HeLa cells.

FIG. 2D shows RT-PCR transcripts from wild-type and ΔSTX17 HeLa cells.

Figure 2E:
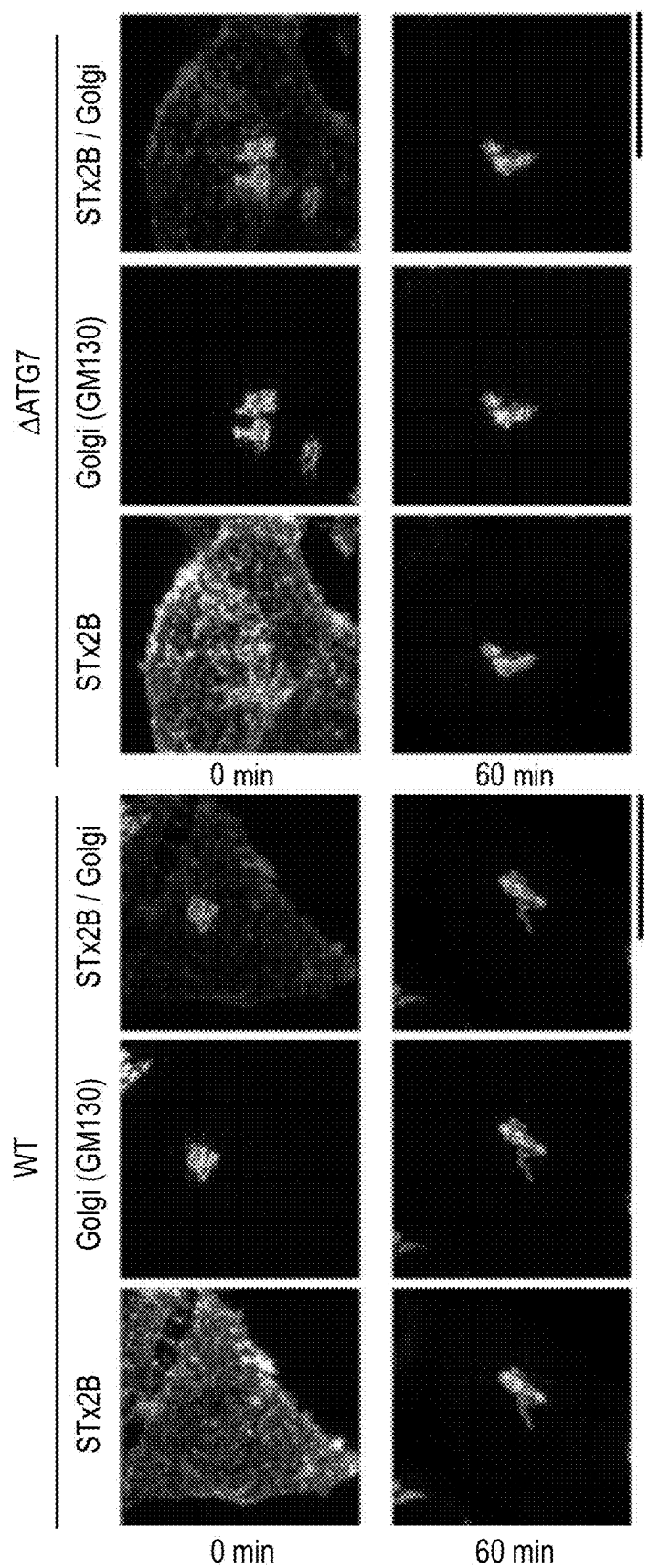

FIG. 2E shows STx2B transport imaged in wild-type and ΔATG7 HeLa cells at 0 or 60 min. Scale bars, 25 μm.

Figure 2F:
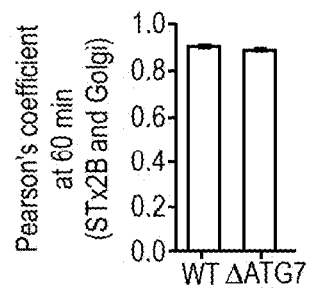

FIG. 2F shows the Pearson's coefficient for colocalization between STx2B and the Golgi apparatus at 60 min from FIG. 2E. N=15 cells per condition. There were no differences between groups using t-test.

Figure 2G:
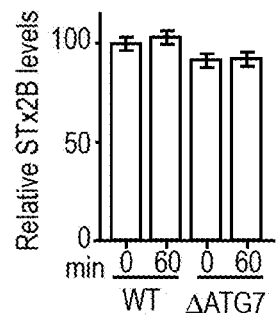

FIG. 2G shows STx2B levels from FIG. 2E. Levels at 0 min in WT cells (G and J) or cells transfected with control siRNA (M and P) normalized to 100. N>15 cells per condition. There were no differences between WT or control siRNA-transfected cells at 0 min and other groups using one-way ANOVA and Dunnett's post hoc test.

Figure 2H:
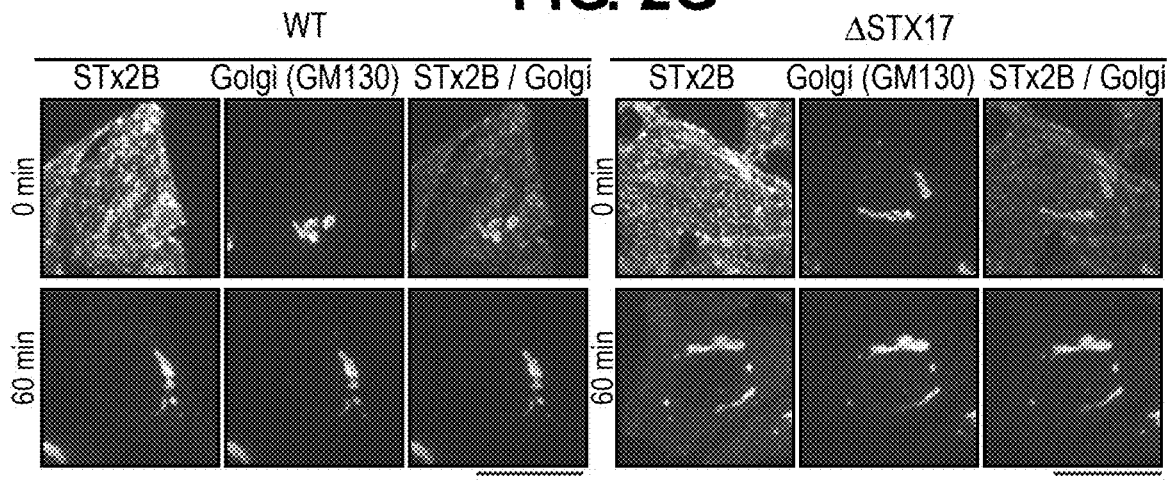

FIG. 2H shows STx2B transport imaged in wild-type and ΔSTX17 HeLa cells at 0 or 60 min. Scale bars, 25 μm.

Figure 2I:
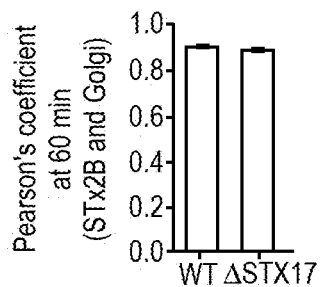

FIG. 2I shows the Pearson's coefficient for colocalization between STx2B and the Golgi apparatus at 60 min from FIG. 2H. N=15 cells per condition. There were no differences between groups using t-test.

Figure 2J:
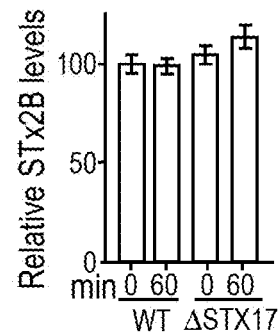

FIG. 2J shows STx2B levels from FIG. 2H. Levels at 0 min in WT cells (G and J) or cells transfected with control siRNA (M and P) normalized to 100. N>15 cells per condition. There were no differences between WT or control siRNA-transfected cells at 0 min and other groups using one-way ANOVA and Dunnett's post hoc test.

Figure 2K:
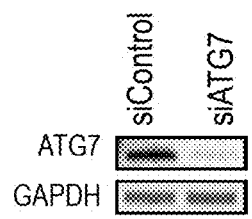

FIG. 2K shows RT-PCR transcripts from HeLa cells transfected with ATG7 siRNA.

Figure 2L:
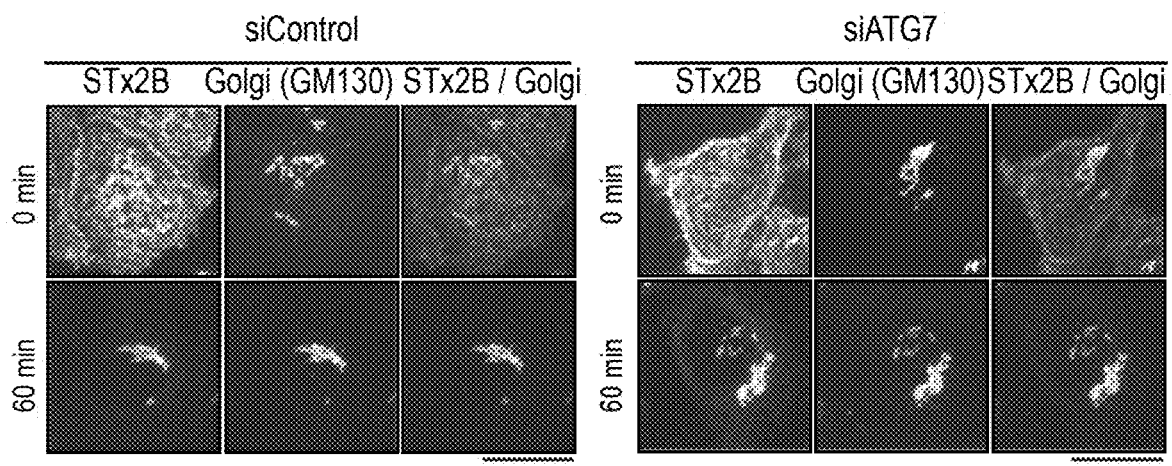

FIG. 2L shows STx2B transport imaged in HeLa cells transfected with ATG7 siRNA at 0 or 60 min. Scale bars, 25 μm.

Figure 2M:
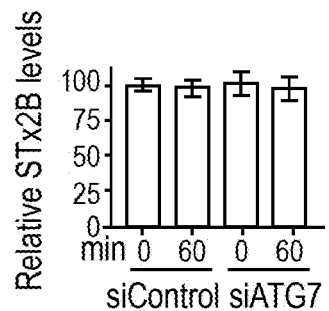

FIG. 2M shows STx2B levels from FIG. 2L. Levels at 0 min in WT cells (G and J) or cells transfected with control siRNA (M and P) normalized to 100. N>15 cells per condition. There were no differences between WT or control siRNA-transfected cells at 0 min and other groups using one-way ANOVA and Dunnett's post hoc test.

Figure 2N:
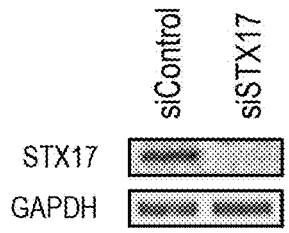

FIG. 2N shows RT-PCR transcripts from HeLa cells transfected with STX17 siRNA.

Figure 2O:
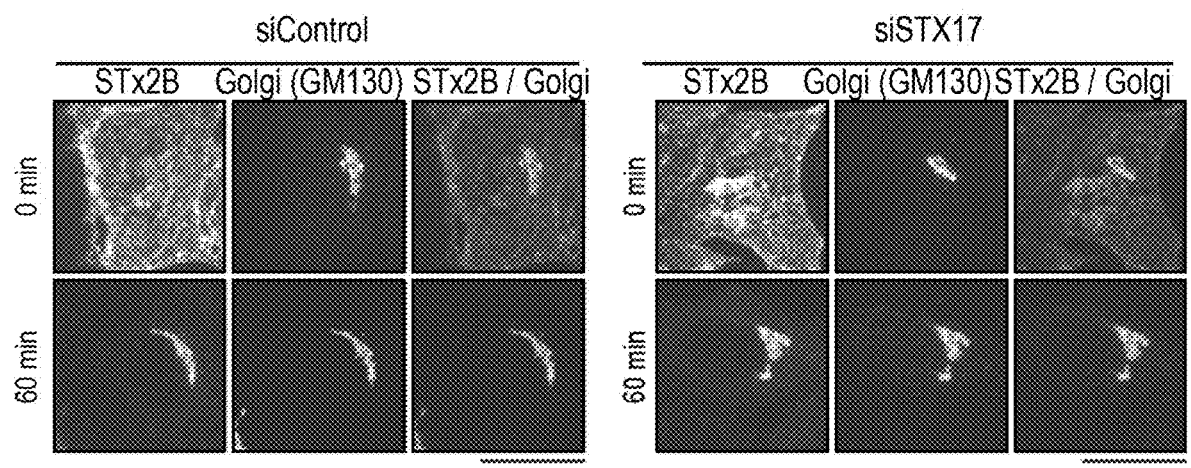

FIG. 2O shows STx2B transport imaged in HeLa cells transfected with STX17 siRNA at 0 or 60 min. Scale bars, 25 μm.

Figure 2P:
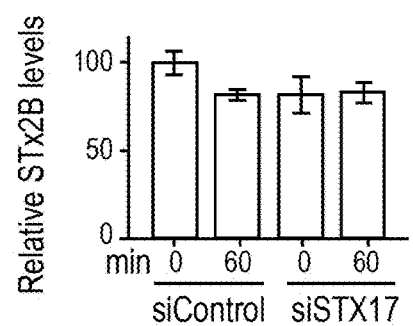

FIG. 2P shows STx2B levels from FIG. 2O. Levels at 0 min in WT cells (G and J) or cells transfected with control siRNA (M and P) normalized to 100. N>15 cells per condition. There were no differences between WT or control siRNA-transfected cells at 0 min and other groups using one-way ANOVA and Dunnett's post hoc test. Taken together, FIGS. 2A-2P show that the autophagy pathway is not required for STx2B trafficking.

Figure 3A:

FIG. 3A shows RT-PCR transcripts from HeLa cells with or without transfection with Vps39 siRNA.

Figure 3B:
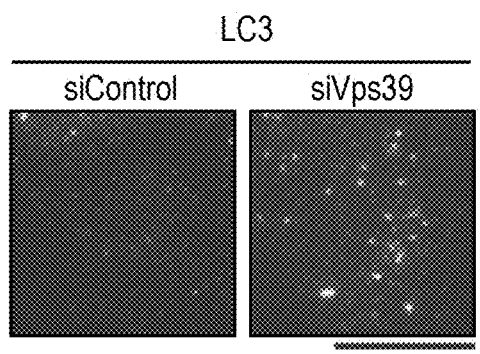

FIG. 3B shows immunofluorescence to detect LC3 in HeLa cells transfected with Vps39 siRNA. Scale bars, 25 μm.

Figure 3C:
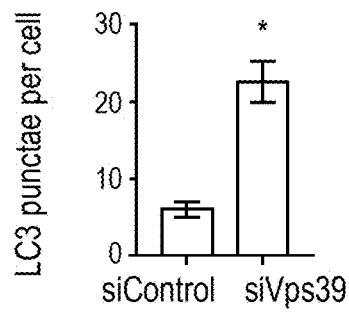

FIG. 3C shows the quantification of LC3 punctae from FIG. 3B. N≥15 cells per condition. *p<0.05 by t-test.

Figure 3D:
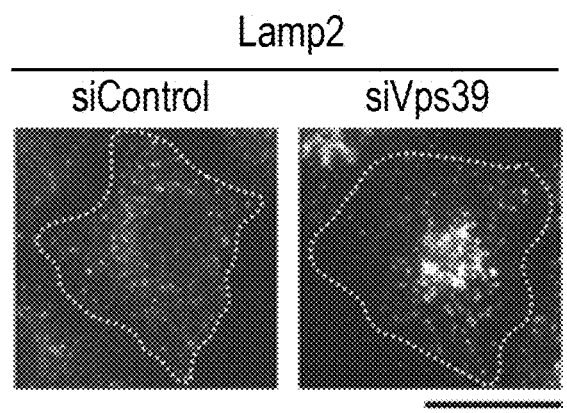

FIG. 3D shows immunofluorescence to detect Lamp2 in HeLa cells transfected with Vps39 siRNA. Scale bars, 25 μm.

Figure 3E:
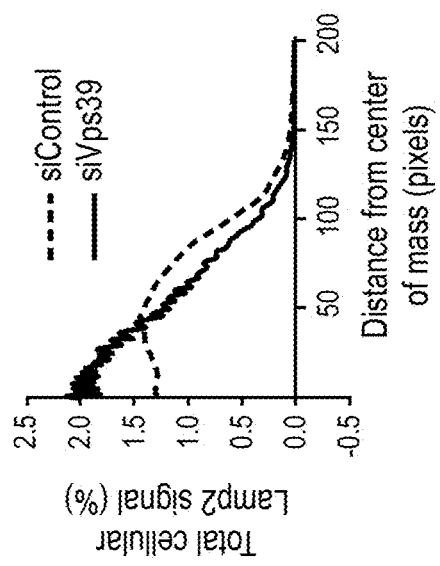

FIG. 3E shows the quantification of data from FIG. 2D. N≥15 cells per condition. *p<0.05 by t-test.

Figure 3F:
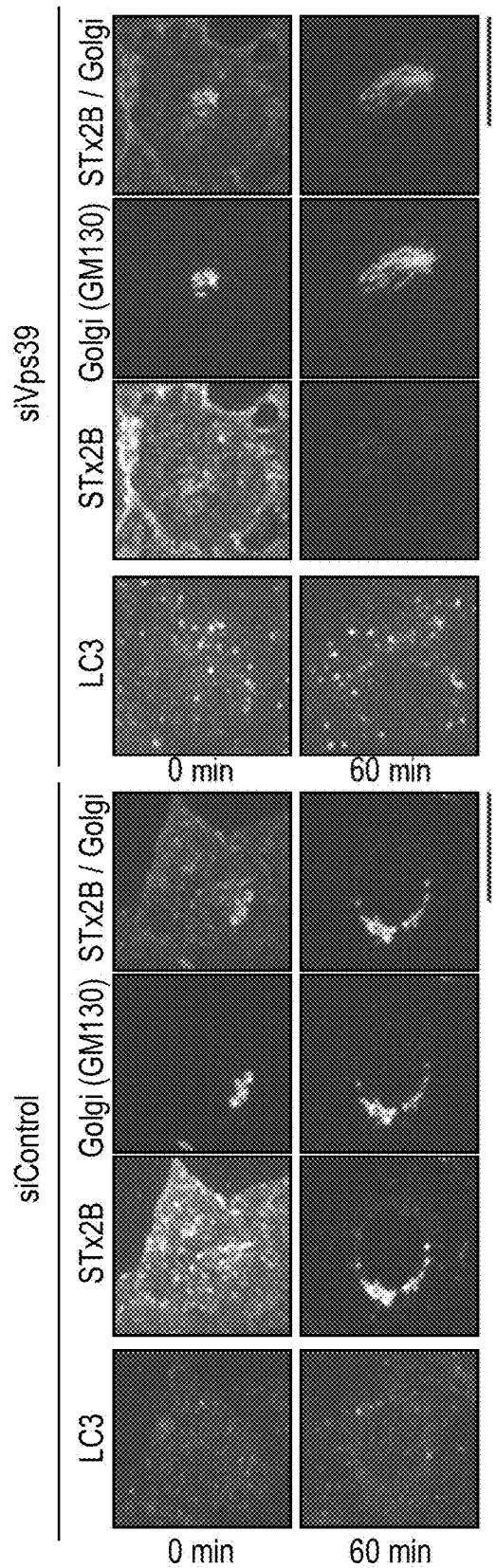

FIG. 3F shows STx2B transport in HeLa cells transfected with Vps39 siRNA. Scale bars, 25 μm.

Figure 3G:
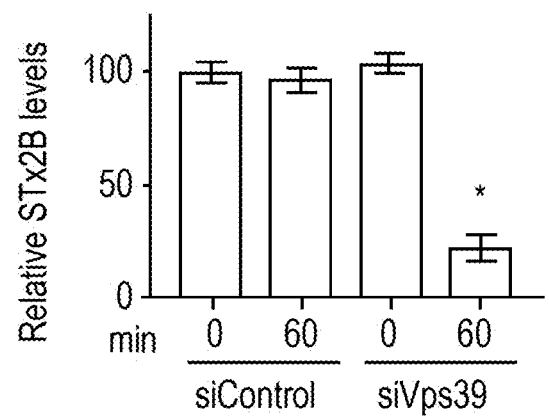

FIG. 3G shows the relative STx2B levels from FIG. 3F. Levels in control-transfected cells at 0 min normalized to 100. N=15 cells per condition. *p<0.05 by one-way ANOVA and Dunnett's post hoc test for the comparison between control 0 min and other groups.

Figure 3H:
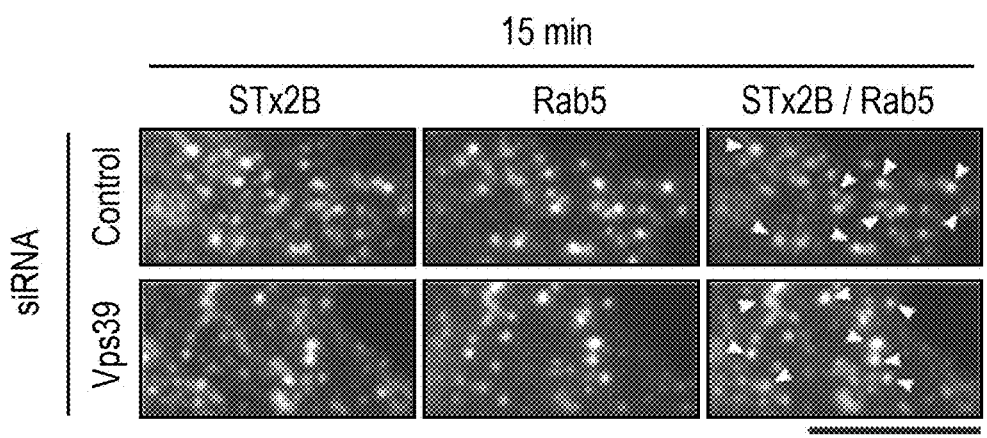

FIG. 3H shows STx2B transport in cells transfected with control or Vps39 siRNA. Cells were also transfected with plasmids encoding $Rab5_{WT}$ 24 h prior to the transport assay. Scale bars, 10 μm.

Figure 3I:
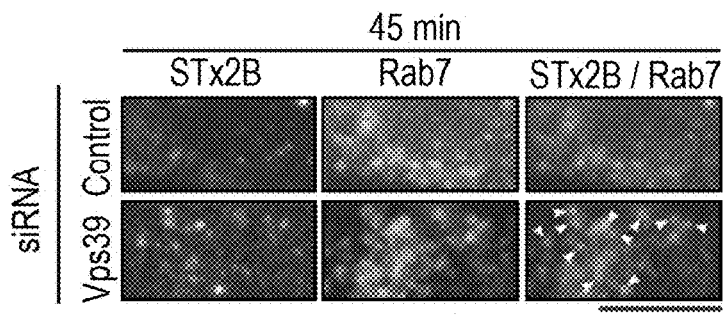

FIG. 3I shows STx2B transport in cells transfected with control or Vps39 siRNA. Cells were also transfected with plasmids encoding $Rab7_{WT}$ 24 h prior to the transport assay. Scale bars, 10 μm.

Figure 3J:
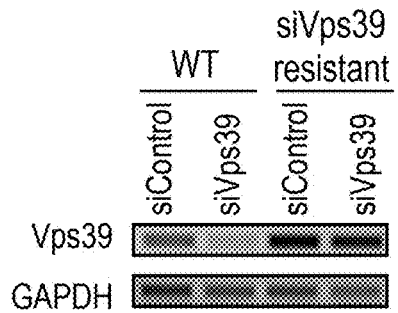

FIG. 3J shows RT-PCR transcripts in WT cells or cells stably overexpressing siRNA-resistant Vps39 after treatment with control or Vps39 siRNA.

Figure 3K:
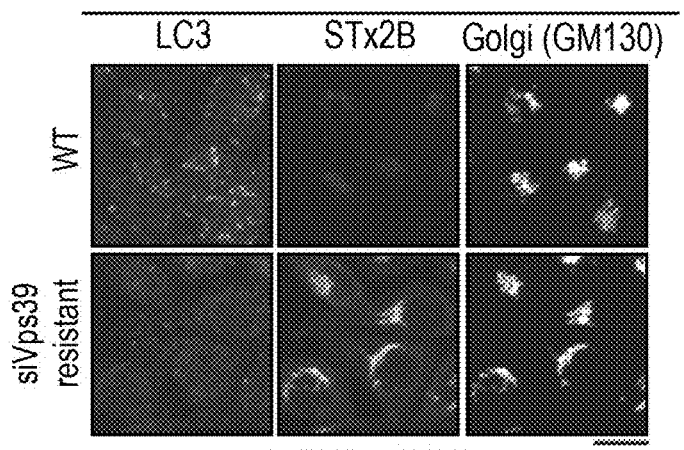

FIG. 3K shows STx2B transport at 60 min in WT cells or cells stably overexpressing siRNA-resistant Vps39 after treatment with Vps39 siRNA. Scale bar, 25 μm.

Figure 3L:
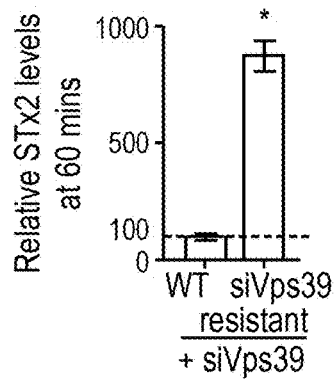

FIG. 3L shows STx2B levels from K. Levels in WT cells normalized to 100. N≥30 cells per condition. *p<0.05 by t-test. Scale bar, 25 μm.

Figure 3M:
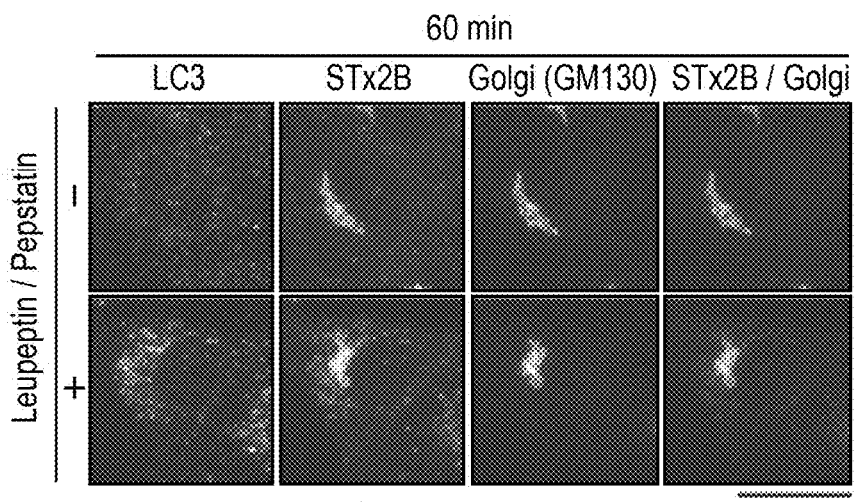

FIG. 3M shows STx2B transport assays in cells treated with or without leupeptin and pepstatin for 24 h. Scale bar, 25 μm.

Figure 3N:
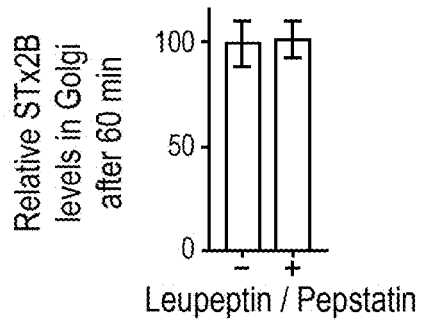

FIG. 3N shows the quantification of the relative amounts of STx2B in the Golgi apparatus from M with values in cultures not exposed to leupeptin/pepstatin normalized to 100. N=15 cells per condition.

Figure 3O:
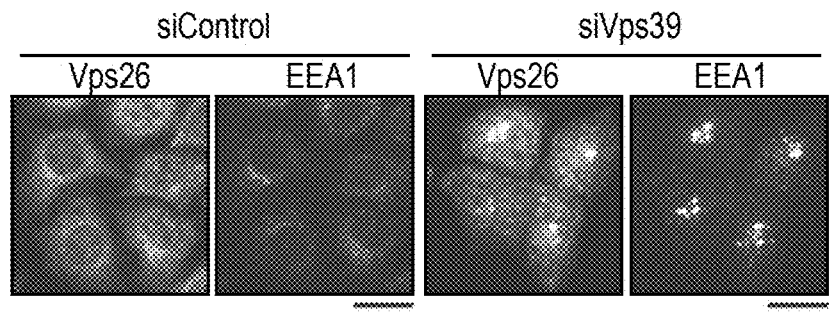

FIG. 3O shows EEA1-positive early endosomes visualized by immunofluorescence in Vps39 knockdown cells. Scale bar, 25 μm.

Figure 3P:
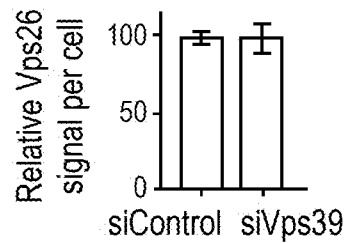

FIG. 3P shows the quantification of relative Vps26 per cell from FIG. 3O. N=15 cells per condition. *p<0.05 by t-test.

Figure 3Q:
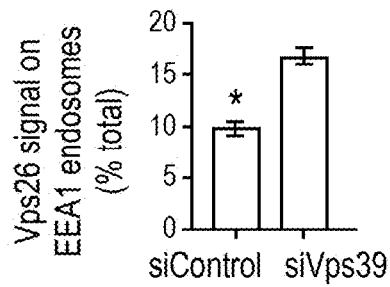

FIG. 3Q shows the quantification of Vps26 signal on EEA1 endosomes in FIG. 3O. N=15 cells per condition. *p<0.05 by t-test.

Figure 3R:
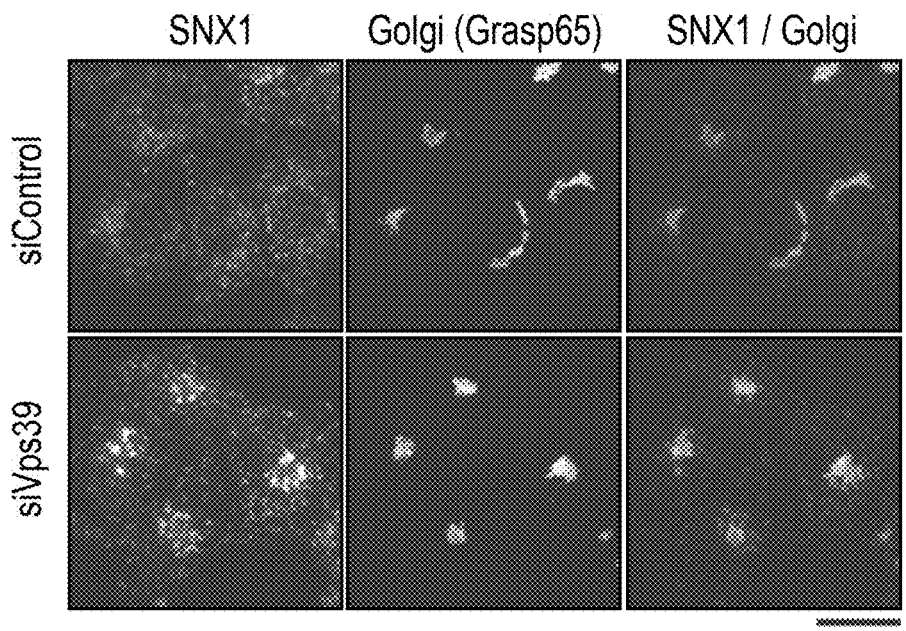

FIG. 3R shows SNX1-positive early endosomes visualized by immunofluorescence in Vps39 knockdown cells. Scale bar, 25 μm.

Figure 3S:
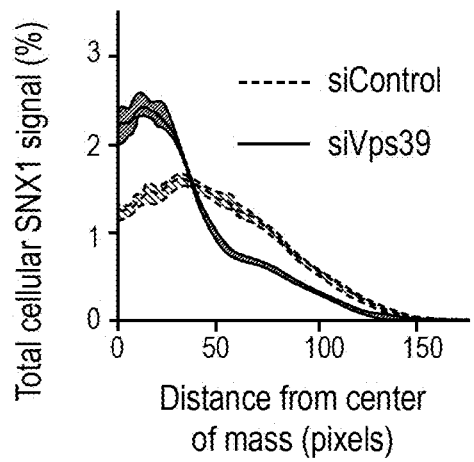

FIG. 3S shows the quantification of data from FIG. 3R. N=15 cells per condition. *p<0.05 by t-test.

Figure 3T:
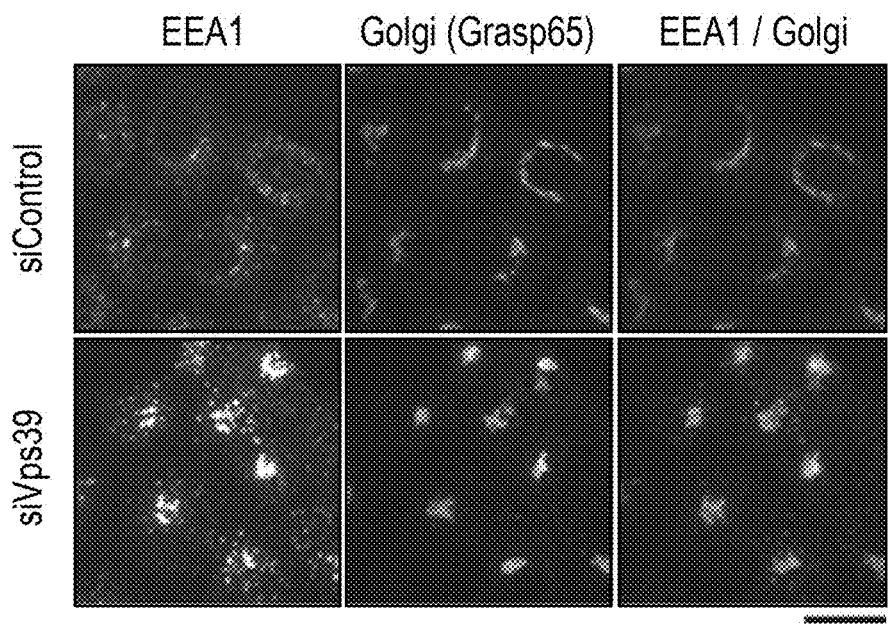

FIG. 3T shows EEA1-positive early endosomes visualized by immunofluorescence in Vps39 knockdown cells. Scale bar, 25 μm.

Figure 3U:
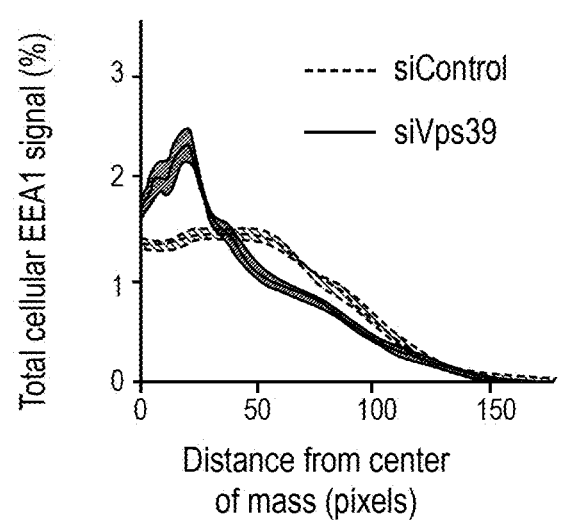

FIG. 3U shows the quantification of data from FIG. 3T. N=15 cells per condition. *p<0.05 by t-test. Taken together, FIGS. 3A-3T shows that depletion of Vps39 blocks the early endosome-to-Golgi transport of STx2B.

Figure 4A:
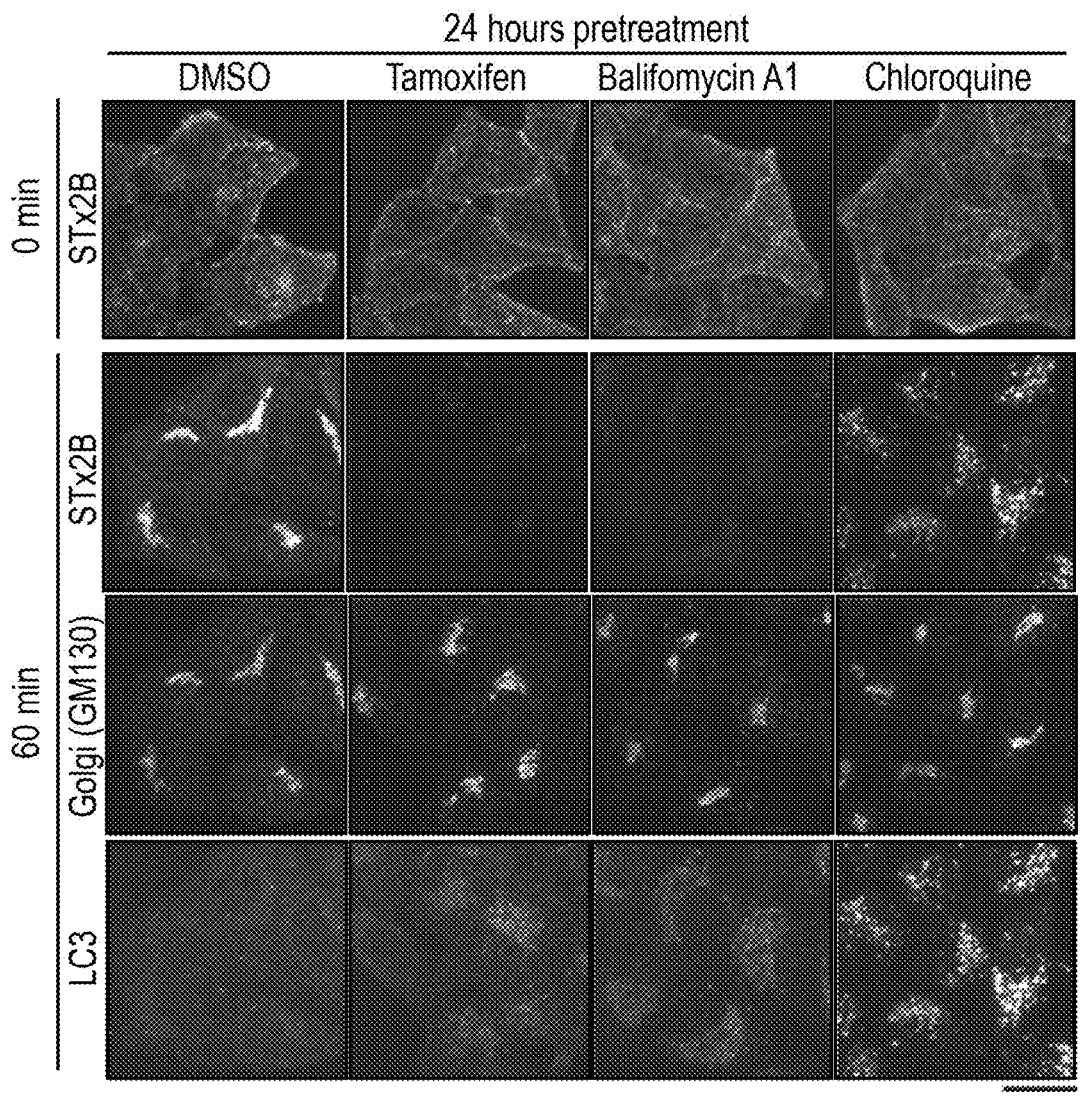

FIG. 4A shows STx2B transport in cells treated with DMSO (0.1%), tamoxifen (10 μm), bafilomycin A1 (100 nM), or chloroquine (50 μM) for 24 h. Scale bar, 25 μm.

Figure 4B:
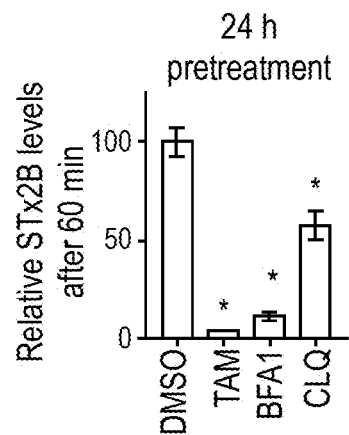

FIG. 4B shows the quantification of data from FIG. 4A with levels in DMSO-exposed cells at 60 min normalized to 100. TAM, tamoxifen; BFA1, bafilomycin A1; CLQ, chloroquine. N=25 cells per condition. *p<0.05 by one-way ANOVA and Dunnett's post hoc test for comparison between DMSO and other groups.

Figure 4C:
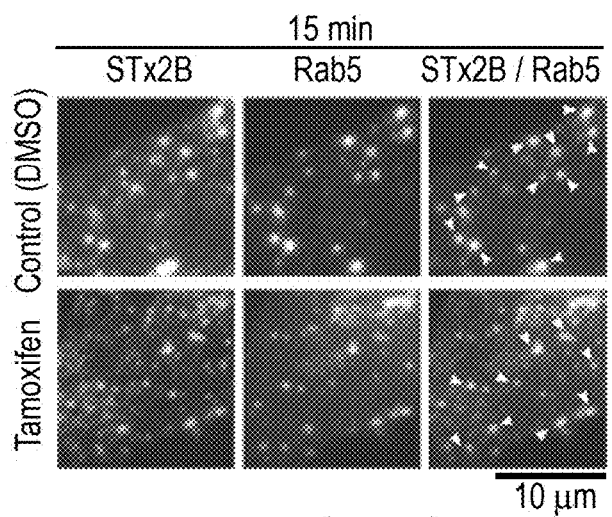

FIG. 4C shows STx2B transport in cells transfected with $Rab5_{WT}$ for 24 h and subsequently treated with 10 μM DMSO or tamoxifen for an additional 24 h. Scale bars, 10 μm.

Figure 4D:
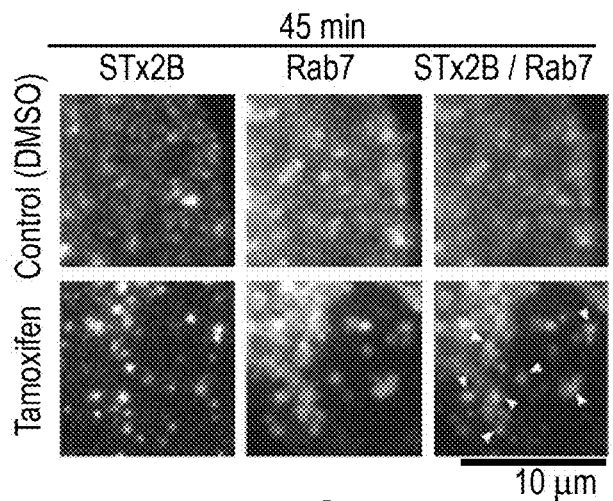

FIG. 4D shows STx2B transport in cells transfected with $Rab7_{WT}$ for 24 h and subsequently treated with 10 μM DMSO or tamoxifen for an additional 24 h. Scale bars, 10 μm.

Figure 4E:
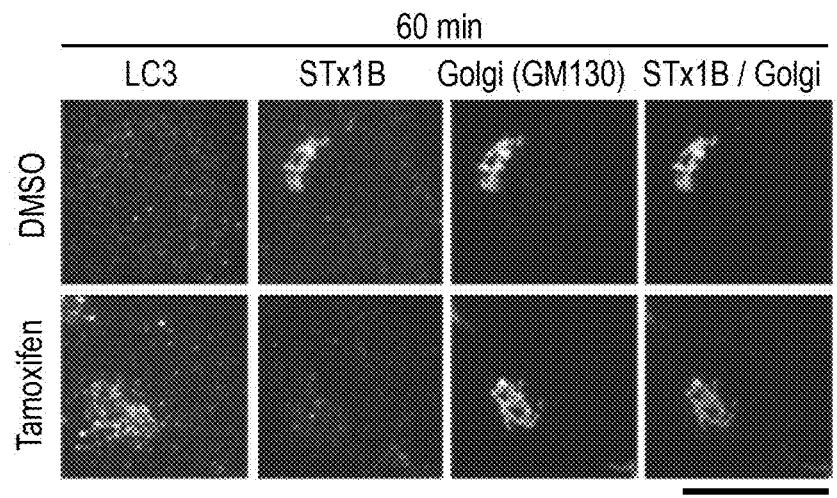

FIG. 4E shows STx1B transport in cells treated with DMSO or 10 μM tamoxifen for 24 h. Scale bar, 25 μm.

Figure 4F:
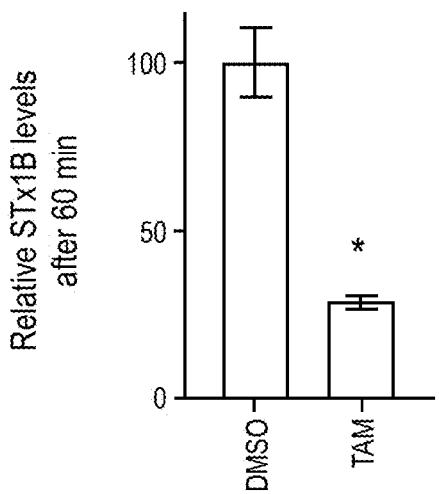

FIG. 4F shows the quantification from E as described for B. N>15 cells. *p<0.05 by t-test. Taken together, FIGS. 4A-4F show that tamoxifen inhibits retrograde trafficking of STx2B and STx1B.

Figure 5A:
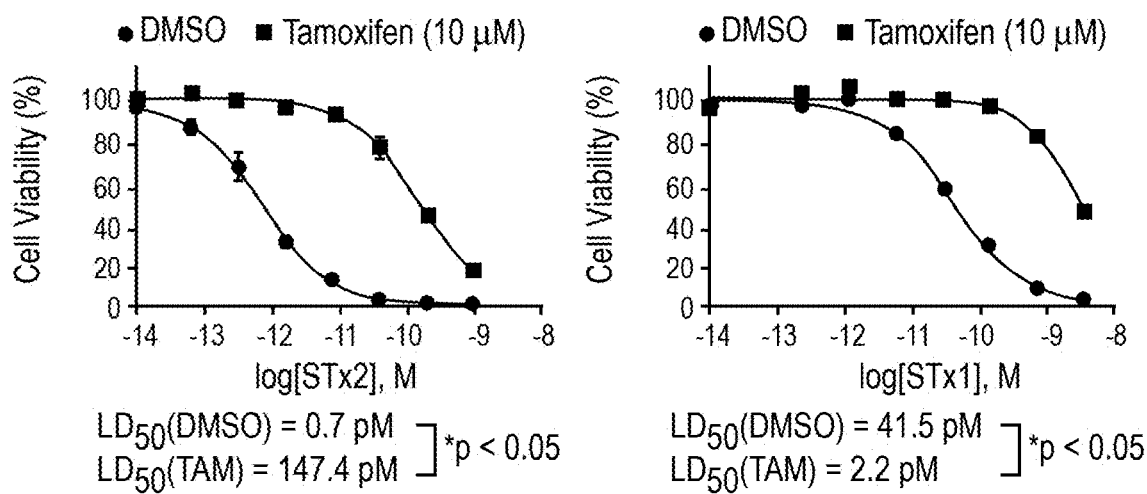

FIG. 5A shows the results of viability assays in cells treated with vehicle or 10 μM tamoxifen for 24 h followed by exposure to indicated concentrations of STx1 or STx2 for 16 h in presence of vehicle or tamoxifen. TAM, tamoxifen. N=3. *p<0.05 by non-linear regression.

Figure 5B:
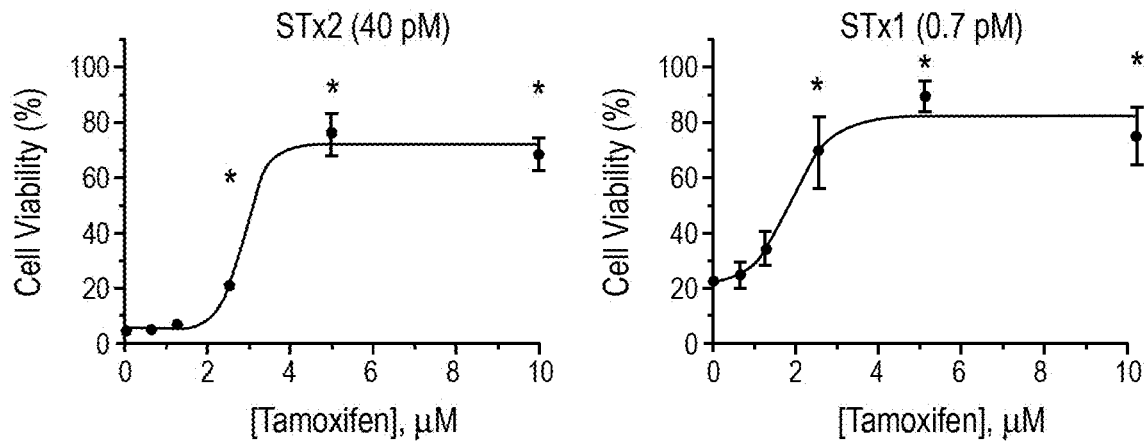

FIG. 5B shows the results of viability assays as in FIG. 5A, using varying concentrations of tamoxifen and 40 μM STx2 or 0.7 nM STx1. N≥3. *p<0.05 by one way ANOVA and Dunnett's post hoc test for comparison between no tamoxifen and other conditions.

Figure 5C:
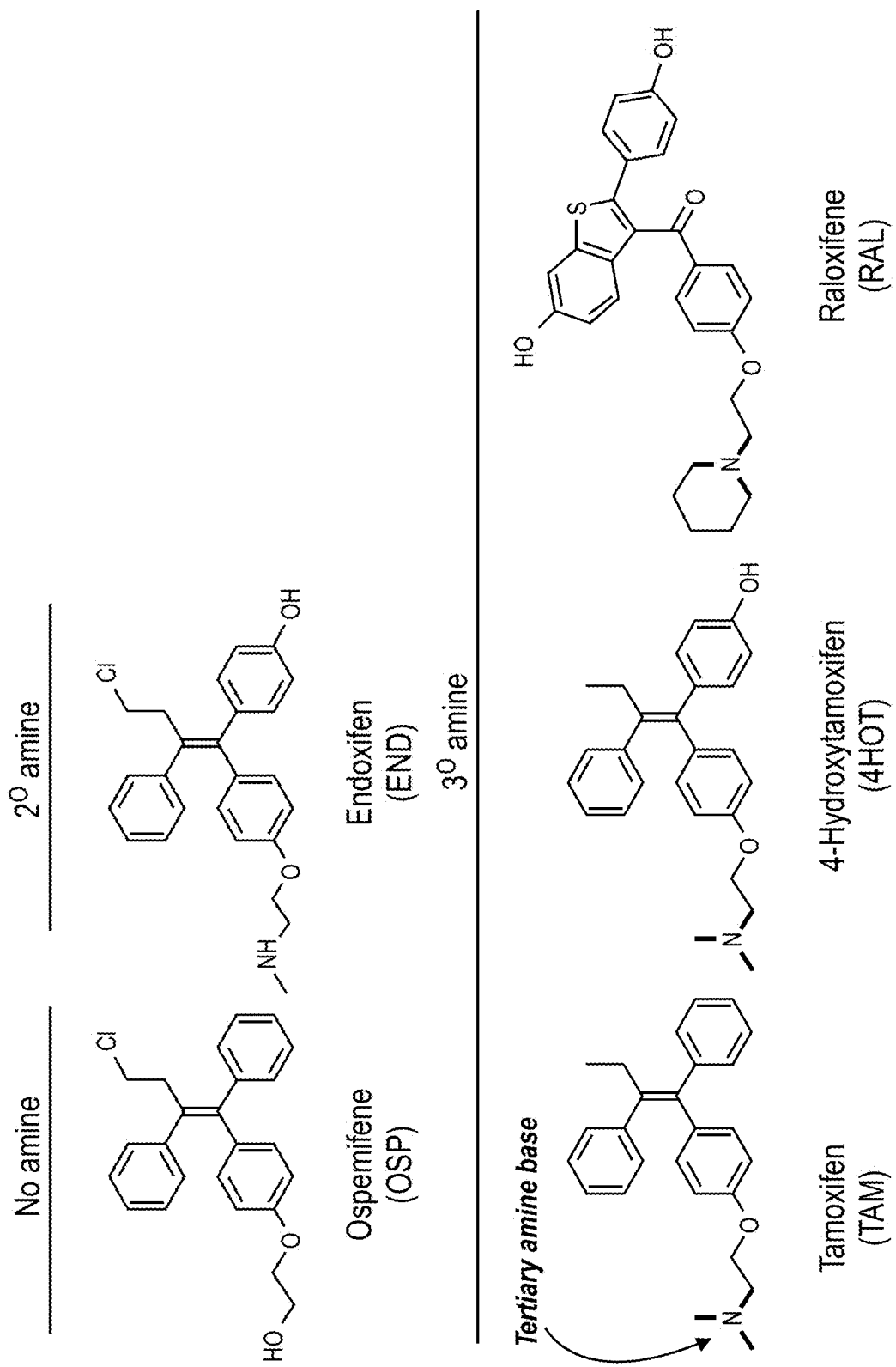
Figure 5C:
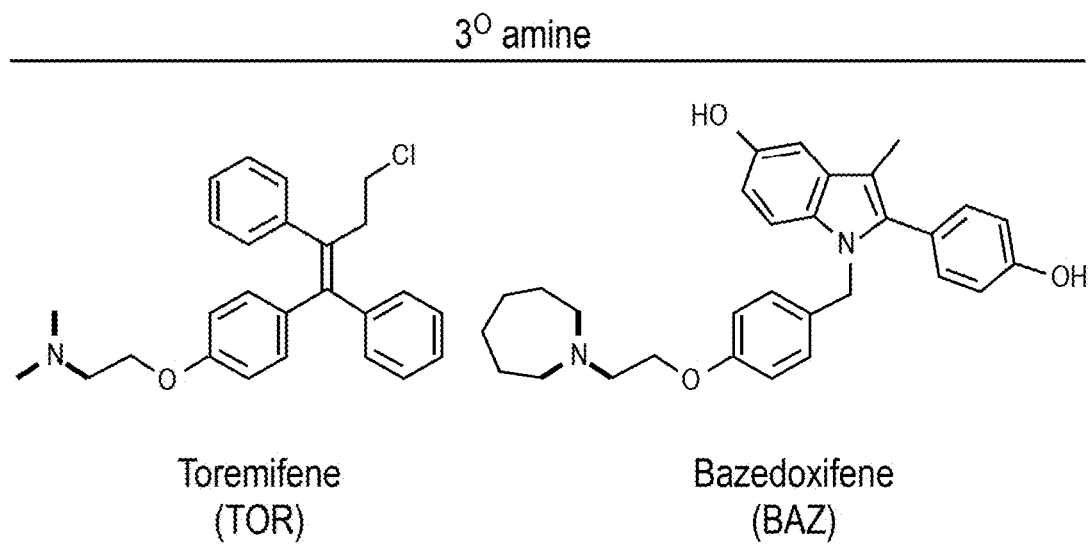

FIG. 5C shows the chemical structures of ospemifene, endoxifen, tamoxifen, 4-hydroxytamoxifen, raloxifene, toremifene, and bazedoxifene.

Figure 5D:
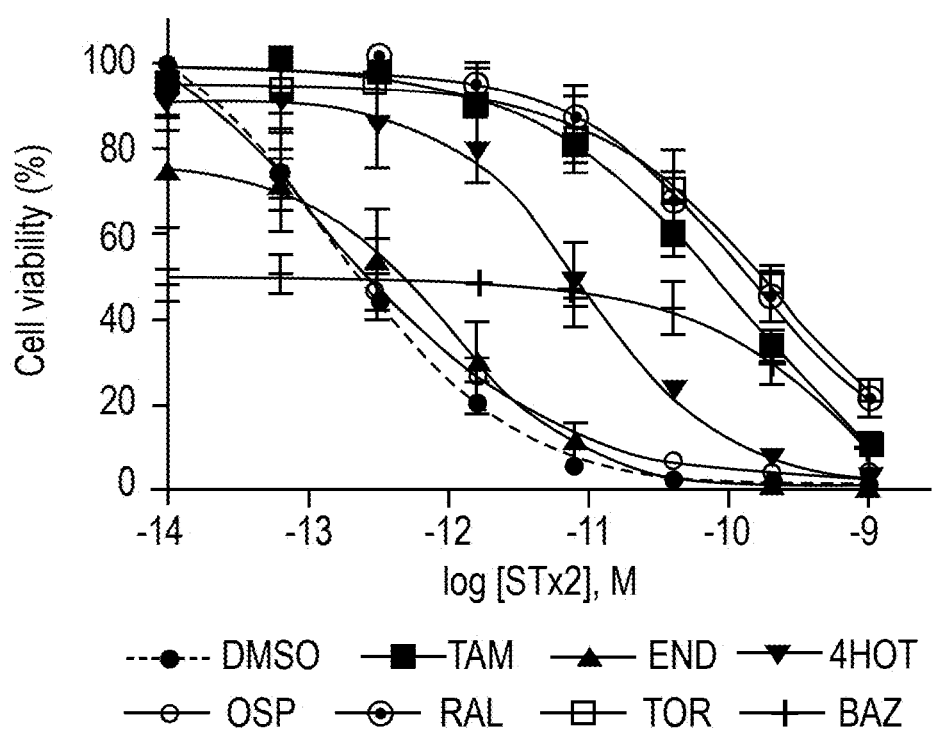

FIG. 5D shows the results of viability assays as in FIG. 5A, using 10 μM of each compound and the indicated concentrations of STx2. $LD_{50}$ with 95% confidence interval depicted in E. N≥3 per compound. *p<0.05 by non-linear regression. N.S.—not significant.

Figure 5E:
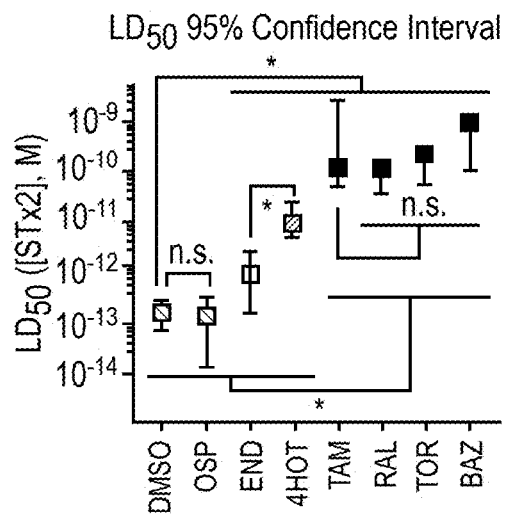

FIG. 5E shows the results of viability assays as in FIG. 5A, using 10 μM of each compound and the indicated concentrations of STx2. $LD_{50}$ with 95% confidence interval depicted in E. N≥3 per compound. *p<0.05 by non-linear regression. N.S.—not significant.

Figure 5F:
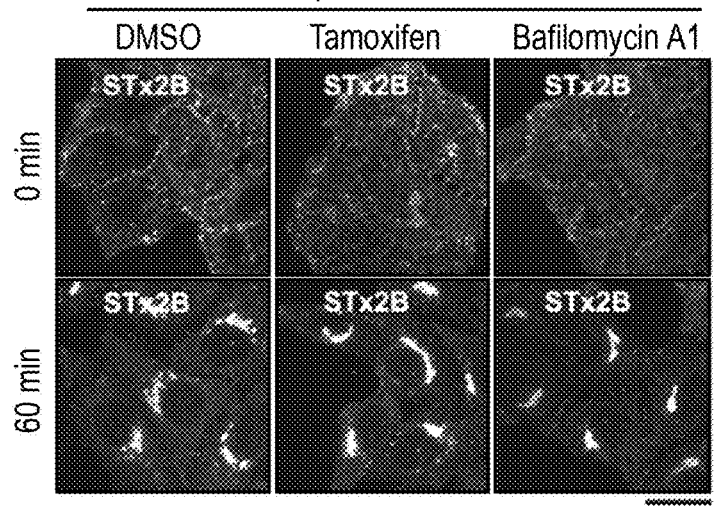

FIG. 5F shows STx2B transport after treatment with the indicated compounds for 4 h. Scale bars, 25 μm.

Figure 5G:
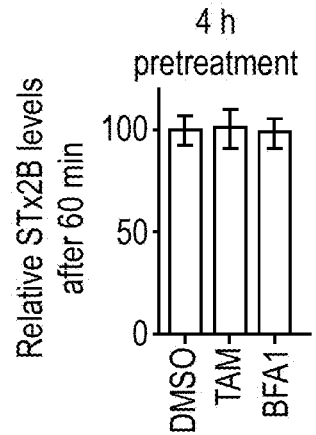

FIG. 5G shows the quantification of data from FIG. 5F with levels in DMSO-exposed cells at 60 min normalized to 100. TAM, tamoxifen; BFA1, bafilomycin A1. N>15 cells per condition. There were no differences between groups using one-way ANOVA.

Figure 5H:
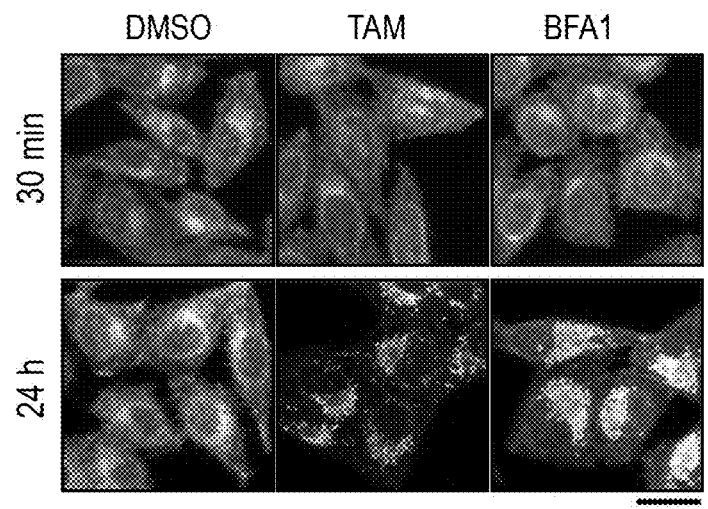

FIG. 5H shows Lysosensor signal in cells treated with the indicated compounds for 30 min or 24 h. Scale bars, 25 μm.

Figure 5I:
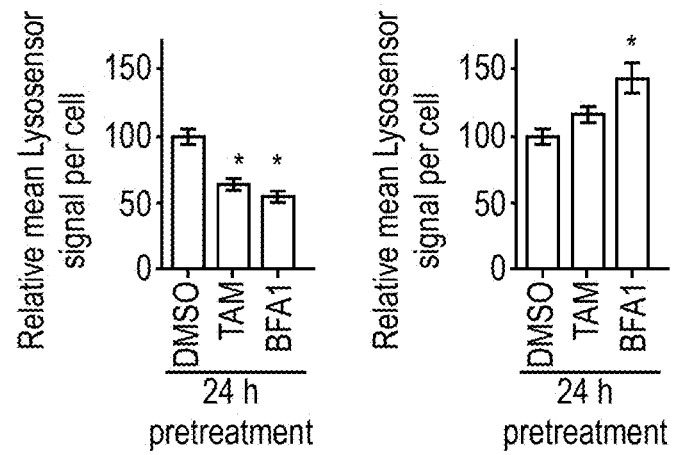

FIG. 5I shows the quantification of mean Lysosensor signal per cell from H. N≥15 cells per condition. *p<0.05 by one-way ANOVA and Dunnett's post hoc test for comparison between DMSO and other groups.

Figure 5J:
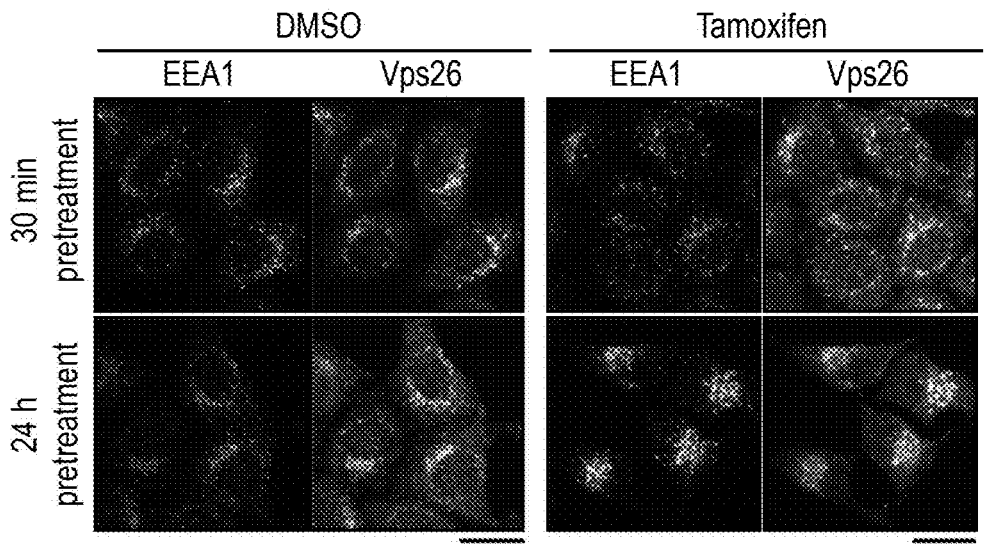

FIG. 5J shows detection of EEA1 and Vps26 via immunofluorescence in cultures exposed to DMSO or 10 μM tamoxifen for 30 min or 24 h. Scale bars, 25 μm.

Figure 5K:
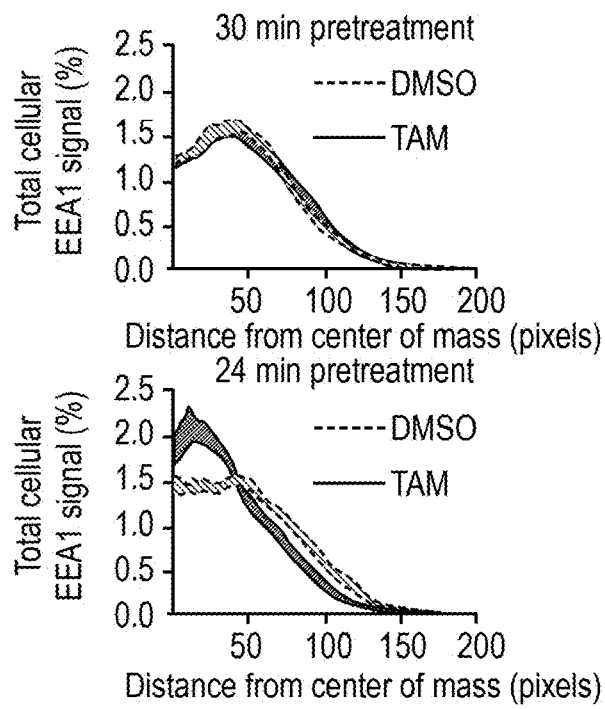

FIG. 5K shows the quantification of total cellular EEA1 signal from FIG. 5I. N=15 cells per condition. *p<0.05 by t-test.

Figure 5L:
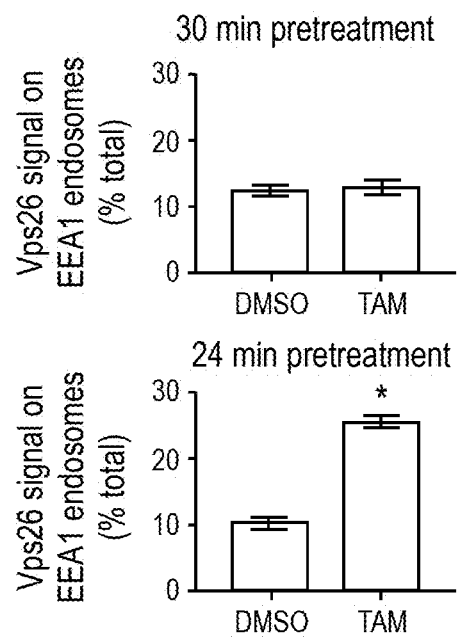

FIG. 5L shows the quantification of Vps26 signal on EEA1 endosomes from FIG. 5I. N=15 cells per condition. *p<0.05 by t-test.

Figure 5M:
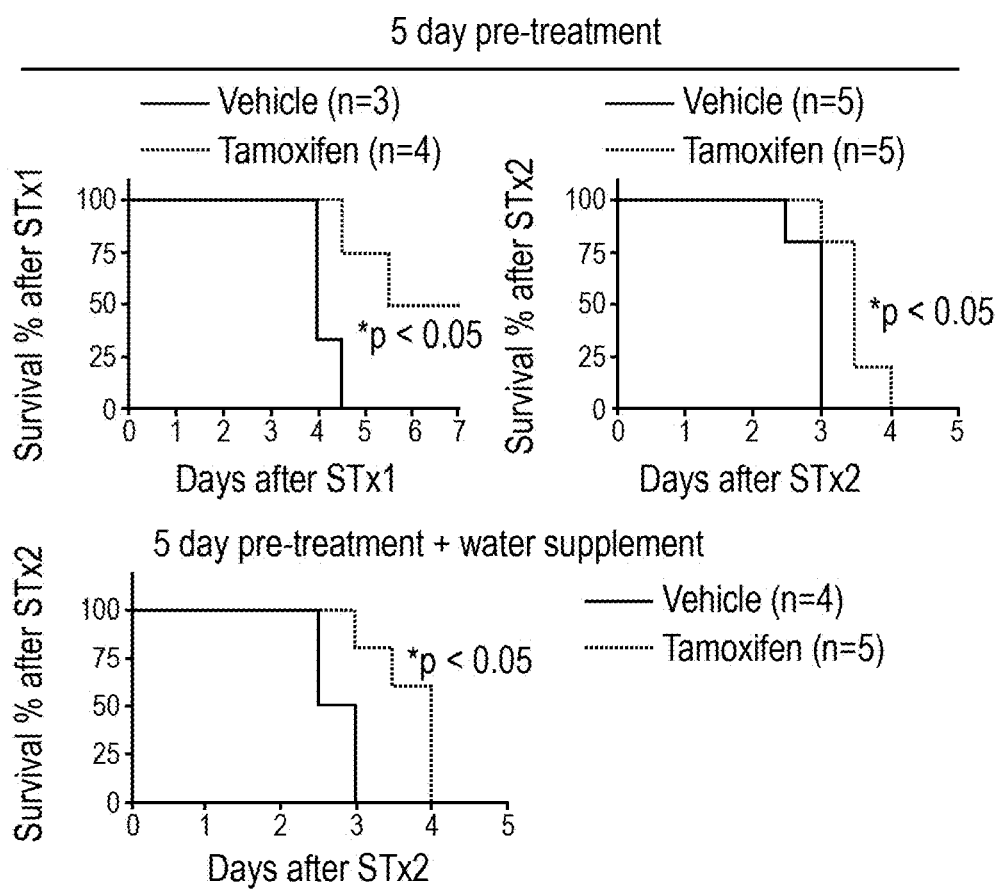

FIG. 5M shows mouse survival assessed by the method of Kaplan Meier. *p<0.05 by the Gehan-Breslow-Wilcoxon and Log-rank (Mantel-Cox) tests. Taken together, FIGS. 5A-5M show that tamoxifen acts as a weak base to protect cells and mice against lethal STx1 or STx2 toxicosis.

DETAILED DESCRIPTION OF THE INVENTION

The present invention is based in part on the unexpected finding, informed by data from a genome-wide siRNA screen, that early endosome-to-Golgi transport of STx2 requires efficient fusion of late endosomes with lysosomes. Inhibition of late endosome-lysosome fusion alters endosomal recruitment of retromer, which is required for the early endosome-to-Golgi transport of STx2, providing a possible explanation for the effects on toxin trafficking. Through a subsequent screen of clinically-approved drugs that target lysosomes, tamoxifen was identified as a potent inhibitor of the early endosome-to-Golgi transport and toxicity of STx2 and STx1. Further, it was found that tamoxifen acts as a weak base to increase endolysosomal pH, which alters endosomal dynamics and impacts endosomal recruitment of retromer. Importantly, tamoxifen increases the survival of mice exposed to lethal STx2 or STx1, in contrast to other active agents that were previously known to affect STx1-mediated toxicity alone. These findings identify a previously unknown role for late endosome-lysosome fusion in cargo transport at the early endosome/Golgi interface and show that tamoxifen can be useful for treating STEC infections.

I. Definitions

As used herein, the term "Shiga toxicosis" refers to the accumulation of toxic levels of Shiga toxin in a subject, resulting in symptoms such as severe diarrhea, abdominal pain, vomiting, bloody urine, and low-grade fever. Shiga toxicosis can lead to conditions such as dysentery, hemorrhagic colitis, hemolytic uremic syndrome, and postdiarrheal thrombotic thrombocytopenic purpura.

As used herein, the term "Shiga toxin" refers to multisubunit proteins, originally isolated from bacteria such as *Shigella* and *Escherichia* species, that inhibit protein synthesis in sensitive eukaryotic cells. Shiga toxins are made up of an A subunit, which interferes with ribosomal activity, and five B subunits which mediate entry of Shiga toxin into cells. The structure and function of Shiga toxins are described, for example, by Sandvig and van Deurs (*EMBOJ.*, 19: 5943-50, 2000) and Melton-Celsa (*Microbiol Spectrum* 2(3):EHEC-0024-2013, 2014). Certain *E. coli* strains produce one or two types of Shiga toxins, referred to as Stx1 and Stx2.

As used herein, the terms "treat," "treatment," and "treating" refer to any indicia of success in the treatment or amelioration of an injury, pathology, condition, or symptom (e.g., diarrhea), including any objective or subjective parameter such as abatement; remission; diminishing of symptoms or making the symptom, injury, pathology or condition more tolerable to the patient; reduction in the rate of symptom progression; decreasing the frequency or duration of the symptom or condition; or, in some situations, preventing the onset of the symptom. The treatment or amelioration of symptoms can be based on any objective or subjective parameter, including, e.g., the result of a physical examination.

As used herein, the term "tamoxifen" refers to (Z)-2-(4-(1,2-diphenyl-1-butenyl) phenoxy)-N,N-dimethylethan-1-amine as shown in FIG. 5C.

As used herein, the term "4-hydroxytamoxifen" refers to (Z)-4-(1-(4-(2-(dimethylamino)ethoxy)phenyl)-2-phenyl-but-1-en-1-yl)phenol as shown in FIG. 5C.

As used herein, the term "endoxifen" refers to (Z)-4-(1-(4-(2-(methylamino)ethoxy)phenyl)-2-phenylbut-1-en-1-yl) phenol as shown in FIG. 5C.

As used herein, the term "toremifene" refers to (Z)-2-(4-(4-chloro-1,2-diphenylbut-1-en-1-yl)phenoxy)-N,N-dimethylethan-1-amine as shown in FIG. 5C.

As used herein, the term "raloxifene" refers to (6-hydroxy-2-(4-hydroxyphenyl)benzo[b]thiophen-3-yl)(4-(2-(piperidin-1-yl)ethoxy)phenyl)methanone as shown in FIG. 5C.

As used herein, the term "bazedoxifene" refers to 1-(4-(2-(azepan-1-yl)ethoxy)benzyl)-2-(4-hydroxyphenyl)-3-methyl-1H-indol-5-ol as shown in FIG. 5C.

As used herein, the term "salt" refers to acid or base salts of active agents such as tamoxifen. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, and quaternary ammonium (methyl iodide, ethyl iodide, and the like) salts. It is understood that the pharmaceutically acceptable salts are non-toxic.

The neutral forms of the active agents can be regenerated by contacting the salt with a base or acid and isolating the parent compound in the conventional manner if desired. The parent form of the compound differs from the various salt forms in certain physical properties, such as solubility in polar solvents, but otherwise the salts are equivalent to the parent form of the compound for the purposes of the present disclosure.

As used herein, the terms "effective amount" and "therapeutically effective amount" refer to a dose of a compound such as tamoxifen that produces therapeutic effects for which it is administered and/or reduces the levels of Shiga toxin in a subject. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); Goodman & Gilman's *The Pharmacological Basis of Therapeutics*, 11$^{th}$ Edition, 2006, Brunton, Ed., McGraw-Hill; and *Remington: The Science and Practice of Pharmacy*, 21$^{st}$ Edition, 2005, Hendrickson, Ed., Lippincott, Williams & Wilkins).

As used herein, the term "pharmaceutically acceptable excipient" refers to a substance that aids the administration of an active agent to a subject. By "pharmaceutically acceptable," it is meant that the excipient is compatible with the other ingredients of the formulation and is not deleterious to the recipient thereof. Useful pharmaceutical excipients include, but are not limited to, binders, fillers, disintegrants, lubricants, glidants, coatings, sweeteners, flavors and colors.

As used herein, the terms "about" and "around" indicate a close range around a numerical value when used to modify that specific value. If "X" were the value, for example, "about X" or "around X" would indicate a value from 0.9X to 1.1X, e.g., a value from 0.95X to 1.05X, or a value from 0.98X to 1.02X, or a value from 0.99X to 1.01X. Any reference to "about X" or "around X" specifically indicates at least the values X, 0.9X, 0.91X, 0.92X, 0.93X, 0.94X, 0.95X, 0.96X, 0.97X, 0.98X, 0.99X, 1.01X, 1.02X, 1.03X, 1.04X, 1.05X, 1.06X, 1.07X, 1.08X, 1.09X, and 1.1X, and values within this range.

II. Methods and Composition for the Treatment of Shiga Toxicosis

Provided herein are methods for treating Shiga toxicosis. The methods include the administration of tamoxifen, 4-hydroxytamoxifen, endoxifen, toremifene, raloxifene, bazedoxifene, a pharmaceutically acceptable salt thereof, or combinations thereof to subjects infected with or otherwise exposed to Shiga toxin-producing bacteria. As described in more detail below, administration of these compounds has been discovered to inhibit early endosome-to-Golgi transport of Shiga toxin 1 and/or Shiga toxin 2. In some embodiments, the active gent is selected from the group consisting of tamoxifen, toremifene, and raloxifene. In some embodiments, the active agent is tamoxifen.

In some embodiments, the subject is infected with a Shiga toxin-producing *Escherichia* species (e.g., Shiga toxin-producing *E. coli*), a Shiga toxin-producing *Shigella* species (e.g., *S. dysenteriae*), or a combination thereof. In some embodiments, the subject is infected with Shiga toxin-producing *E. coli*, also referred to as STEC. Examples of STEC include, but are not limited to, *E.coli* O157:H7, *E.coli* O26:H11, *E.coli* O45:H2, *E.coli* O103:H11, *E.coli* O111, *E.coli* O121:H19, *E.coli* O145, and *E.coli* O104:H4. *E. coli* O157:H7 in particular, which is present in the gastrointestinal tract of healthy cattle, is known as a prevalent foodborne pathogens. *E. coli* O157:H7 can express Stx1 only, Stx2 only, or both toxins.

Shiga toxin-producing bacteria such as STEC can be identified, if necessary, in a sample obtained from a subject (e.g., a stool sample or other specimen) using a culture assay, a nonculture assay, or a combination thereof. For example, O157 *E. coli* can distinguished from many other types of normal intestinal *E. coli* by their inability to ferment sorbitol in an agar isolation media such as sorbitol-MacConkey agar. The identity of suspected isolates can be confirmed via agglutination assay with an antibody-coated latex particle reagent (available, for example, from Microgen Bioproducts). Alternatively, immunoassays conducted with products including, but not limited to, Premier EHEC (Meridian Diagnostics, Cincinnati, Ohio) and ProSpecT Shiga Toxin *E. coli* Microplate Assay (Remel, Lenexa, KS) can be employed, as well as PCR-based assays to detect the stx1 gene and/or stx2 gene. Examples of these and other methods are described, for example, by Gould et al. (Centers for Disease Control and Prevention. Morbidity and Mortality Weekly Report. 2009; 58(No. RR-12):1-13).

A diagnosis of Shiga toxicosis may be made upon the appearance in a subject of one or more signs or symptoms commonly associated with infections caused by Shiga toxin-producing bacteria. Examples of such symptoms include, but are not limited to, enteric symptoms such as diarrhea, hemorrhagic diarrhea containing blood, abdominal cramps, nausea, and vomiting. Some subjects may also exhibit fevers, which may be less than 101° F. (38.5° C.) in many instances. In some cases, the bacterial infection may lead to development of hemolytic uremic syndrome (HUS) in the subject. HUS typically develops around a week after symptoms first begin to appear, and may manifest as fatigue, a loss of color in the cheeks or inside eyelids, and/or a decrease in urination frequency. Decreased kidney function or permanent kidney damage can result from untreated HUS, which is a leading cause of acute renal failure in children as well as some adults.

An active agent such as tamoxifen can be administered to subject orally, intravenously, intramuscularly, intraperitoneally, subcutaneously, intrathecally, intraarterially, nasally, rectally, or via other routes if indicated. In some embodiments, tamoxifen, 4-hydroxytamoxifen, endoxifen, toremifene, raloxifene, bazedoxifene, or a combination thereof is administered orally. Active agents can be administered at any suitable dose in the methods provided herein. In general, an active agent such as tamoxifen is administered at a dose ranging from about 0.1 milligrams to about 1000 milligrams per kilogram of a subject's body weight (i.e., about 0.1-1000 mg/kg). The dose of the active agent can be, for example, about 0.1-1000 mg/kg, or about 1-500 mg/kg, or about 25-250 mg/kg, or about 50-100 mg/kg. The dose of the active agent can be about 1, 2, 3, 4, 5, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950 or 1000 mg/kg. In some embodiments, the active agent (e.g., tamoxifen) is administered in an amount ranging from about 0.1 mg/kg/day to about 100 mg/kg/day. In some embodiments, the active agent (e.g., tamoxifen) is administered in an amount ranging from about 0.1 mg/kg/day to about 1.0 mg/kg/day. The dosages can be varied depending upon the requirements of the patient, the severity of the infection or Shiga toxicosis, the route of administration, and the particular formulation being administered. The dose administered to a patient should be sufficient to result in a beneficial therapeutic response in the patient. The size of the dose will also be determined by the existence, nature, and extent of any adverse side-effects that accompany the administration of the drug in a particular patient. Determination of the proper dosage for a particular situation is within the skill of the typical practitioner. The total dosage can be divided and administered in portions over a period of time suitable to treat to the disease or condition.

An active agent such as tamoxifen can be administered for periods of time which will vary depending upon the nature of the particular disorder, its severity, and the overall condition of the subject to whom the active agent is administered. Administration can be conducted, for example, hourly, every 2 hours, three hours, four hours, six hours, eight hours, or twice daily including every 12 hours, or any intervening interval thereof. Administration can be conducted once daily, or once every 36 hours or 48 hours, once per week, twice per week, or three times per week. Following treatment, a subject can be monitored for changes in his or her condition and for alleviation of the symptoms of the Shiga toxicosis or infection. The dosage of the active agent can either be increased in the event the subject does not respond significantly to a particular dosage level, or the dose can be decreased if an alleviation of symptoms is observed, or if the Shiga toxicosis or infection has been remedied, or if unacceptable side effects are seen with a particular dosage.

Treating Shiga toxicosis according to the methods of present disclosure generally alleviates one or more symptoms as described above, including, but not limited to, stomach cramps, vomiting, diarrhea, and fever. In some embodiments, treating Shiga toxicosis can prevent life-threatening effects such as hemolytic uremic syndrome (HUS). In some embodiments, the active agent (e.g., tamoxifen) is administered to the subject before Shiga toxins enter the bloodstream of the subject. Because Shiga toxins generally enter the bloodstream 10-14 days after infection, administration of the active agent can result in the prevention of Shiga toxicosis and its most serious effects, even though infection with Shiga toxin-producing bacteria was not prevented per se. In some embodiments, the active agent is administered to the subject within ten days of the infection. In some embodiments, the active agent is administered to the subject within 10 days of infection by the Shiga toxin-producing bacteria, e.g., the active agent is administered at 10 days after infection, at 7 days after infection, or at 5 days after infection. In some embodiments, the active agent is administered to the subject within 3 days of the appearance of symptomatic diarrhea in the subject, e.g., the active agent is administered at 3 days after the appearance of symptomatic diarrhea, at 2 days after the appearance of symptomatic diarrhea, at 1 day after the appearance of symptomatic diarrhea, or on the same day as the appearance of symptomatic diarrhea. Treatment may be continued for any amount of time suitable to reduce or eliminate one or more symptoms of Shiga toxicosis, reduce or eliminated one or more symptoms of the infection, or to reduce or eliminate the infection itself. In some embodiments, the treatment is conducted for 3-21 days (e.g., 5-14 days, or 8-10 days).

The methods and compositions described herein also can be administered prophylactically in subjects at risk for infection with STx-producing bacteria, to reduce the risk of developing Shiga toxicosis (e.g., for caregivers at risk during an epidemic). For example, prophylactic administration of an active agent or composition as described herein can be used for preventing enteric symptoms of the infection from occurring, delaying onset of enteric symptoms, lessening the severity of subsequently developed enteric symptoms, preventing development of hemorrhagic colitis, and/or preventing development of HUS in the subject.

Administration of tamoxifen, or other active agents such as toremifene or raloxifene, according to the methods provided may result in the reduction of levels of Stx1 and Stx2 in a subject. For example, the levels of Stx1 or Stx2 may be reduced by from about 25% to about 95%, or from about 35% to about 95%, or from about 40% to about 85%, or from about 40% to about 80% as compared to the corresponding levels Stx1 or Stx2 prior to the first administration of the active agent (e.g., 24 hours prior to the first administration of the active agent).

In some embodiments, the methods further include administering an antibiotic to the subject. Examples antibiotics that can be used in the present methods include, but are not limited to: quinolones (e.g., moxifloxacin, gemifloxacin, ciprofloxacin, oflaxacin, trovafloxacin, sitafloxacin, and the like), β-lactams (e.g., penicillins such as amoxicillin, amoxacilin-clavulanate, piperacillin-tazobactam, penicillin G, and the like; and cephalosporins such as ceftriaxone and the like), macrolides (e.g., erythromycin, azithromycin, clarithromycin, and the like), aminoglycosides (e.g., amikacin, gentamicin, kanamycin, neomycin, netilmicin, tobramycin, and the like), monobactams (e.g., aztreonam and the like). carbapenems (e.g., doripenem, imipenem, meropinem, ertapenem, and the like), thiazolides (e.g., tizoxanidine, nitazoxanidine, RM 4807, RM 4809, and the like), tetracyclines (e.g., tetracycline, minocycline, doxycycline, eravacycline, and the like), lincosamides (e.g., lincomycin, clindamycin, and the like), sulfonamides (e.g., trimethoprim, sulfamethoxazole, and the like), and nitroimidazoles (e.g., metronidazole, satranidazole, and the like). The methods of the present disclosure can include administration of (i) tamoxifen, 4-hydroxytamoxifen, endoxifen, toremifene, raloxifene, bazedoxifene, or a combination thereof, and (ii) one or more (e.g., two, three, four, five, six, or more) such antibiotics. Chlorhexidine (e.g., chlorhexidine digluconate) alone or in combination with a zinc compound (e.g., zinc acetate), can also be used in combination with the administered antibiotics. In some embodiments, the methods can also include administration of an anti-diarrheal agent such as loperamide, diphenoxylate, cholestyramine, or codeine (e.g., codeine sulfate).

In some embodiments, the methods further include administering a manganese compound to the subject. The manganese compound can include one or more ionic forms of manganese (e.g., $Mn^{2+}$), manganese salts, or a manganese amino acid chelates. Manganese salts include organic manganese salts (e.g., manganese carbonate, manganese acetate, manganese citrate, manganese oleate, and manganese oxalate) and inorganic manganese salts (e.g., manganese chloride, manganese borate, manganese nitrate, manganese phosphate, and manganese sulfate). In some embodiments, the amino acid chelate contains a manganese ion bonded to an amino acid. The manganese ion may be bonded, for example, to the carboxylate of the amino acid via a covalent or ionic bond. The α-amino group may bonded to the manganese ion via a coordinate covalent bond. Non-limiting examples of manganese amino acid chelates include manganese ions bound to one or more of arginine, asparagine, cysteine, glutamine, histidine, lysine, ornithine, and tryptophan. In some embodiments, the method includes administration of: (i) tamoxifen, toremifene, raloxifene, or a combination thereof and (ii) manganese chloride, manganese sulfate, or a combination thereof. The manganese compound is generally administered in an amount effective to reduce Shiga toxicosis or to reduce risk of developing Shiga toxicosis. The amount of manganese can range for example, from about 0.002 mg of manganese/kg of body weight (mg/kg) to about 50 mg/kg (e.g., about 0.002-0.01 mg/kg, or about 0.1-1 mg/kg, or about 0.5-1.0 mg/kg, or about 1-10 mg/kg, or about 10-20 mg/kg, or about 20-30 mg/kg, or about 30-40 mg/kg, or about 40-50 mg/kg).

An active agent such as tamoxifen may be administered to the subject before administration of a manganese compound and/or an antibiotic, after administration of the manganese compound and/or the antibiotic, or concurrently with administration of the manganese compound and/or the antibiotic. An active agent such as tamoxifen, 4-hydroxytamoxifen, endoxifen, toremifene, raloxifene, or bazedoxifene may be administered in a composition separate from the manganese compound and/or the antibiotic, or in a composition containing the manganese compound and/or the antibiotic. Also provided herein are compositions containing: (i) tamoxifen, 4-hydroxytamoxifen, endoxifen, toremifene, raloxifene, bazedoxifene, or a combination thereof; (ii), a manganese compound, an antibiotic, or a combination thereof and (iii) one or more pharmaceutically acceptable excipients. The compositions may be formulated, e.g., for oral administration, intravenous administration, intramuscular administration, intraperitoneal administration, subcutaneous administration, intrathecal administration, intraarterial administration, nasal administration, or rectal administration.

The pharmaceutical compositions can be prepared by any of the methods well known in the art of pharmacy and drug delivery. In general, preparation of the compositions includes the step of bringing the active ingredients (e.g., tamoxifen and a manganese compound and/or an antibiotic) into association with a carrier containing one or more accessory ingredients. The pharmaceutical compositions are typically prepared by uniformly and intimately bringing the active ingredients into association with a liquid carrier or a finely divided solid carrier or both, and then, if necessary, shaping the product into the desired formulation. The compositions can be conveniently prepared and/or packaged in unit dosage form.

The pharmaceutical compositions may be in a form suitable for oral use. Suitable compositions for oral administration include, but are not limited to, tablets, troches, lozenges, aqueous or oily suspensions, dispersible powders or granules, emulsions, hard or soft capsules, syrups, elixirs, solutions, buccal patches, oral gels, chewing gums, chewable tablets, effervescent powders, and effervescent tablets. Such compositions can contain one or more agents selected from sweetening agents, flavoring agents, coloring agents, antioxidants, and preserving agents in order to provide pharmaceutically elegant and palatable preparations.

Tablets generally contain the active ingredients in admixture with non-toxic pharmaceutically acceptable excipients, including: inert diluents, such as cellulose, silicon dioxide, aluminum oxide, calcium carbonate, sodium carbonate, glucose, mannitol, sorbitol, lactose, calcium phosphate, and sodium phosphate; granulating and disintegrating agents, such as corn starch and alginic acid; binding agents, such as polyvinylpyrrolidone (PVP), cellulose, polyethylene glycol (PEG), starch, gelatin, and acacia; and lubricating agents such as magnesium stearate, stearic acid, and talc. The tablets can be uncoated or coated, enterically or otherwise, by known techniques to delay disintegration and absorption in the gastrointestinal tract and thereby provide a sustained action over a longer period. For example, a time delay material such as glyceryl monostearate or glyceryl distearate can be employed. Tablets can also be coated with a semipermeable membrane and optional polymeric osmogents according to known techniques to form osmotic pump compositions for controlled release. Compositions for oral administration can be formulated as hard gelatin capsules wherein the active ingredient is mixed with an inert solid diluent (such as calcium carbonate, calcium phosphate, or kaolin), or as soft gelatin capsules wherein the active ingredients are mixed with water or an oil medium (such as peanut oil, liquid paraffin, or olive oil).

The pharmaceutical compositions can also be in the form of an injectable aqueous or oleaginous solution or suspension. Sterile injectable preparations can be formulated using non-toxic parenterally-acceptable vehicles including water, Ringer's solution, and isotonic sodium chloride solution, and acceptable solvents such as 1,3-butane diol. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Aqueous suspensions contain the active agents in admixture with excipients suitable for the manufacture of aqueous suspensions. Such excipients include, but are not limited to: suspending agents such as sodium carboxymethylcellulose, methylcellulose, oleagino-propylmethylcellulose, sodium alginate, polyvinyl-pyrrolidone, gum tragacanth and gum acacia; dispersing or wetting agents such as lecithin, polyoxyethylene stearate, and polyethylene sorbitan monooleate; and preservatives such as ethyl, n-propyl, and p-hydroxybenzoate. Oily suspensions can be formulated by suspending the active ingredients in a vegetable oil, for example, arachis oil, olive oil, sesame oil or coconut oil, or in a mineral oil such as liquid paraffin. The oily suspensions can contain a thickening agent, for example beeswax, hard paraffin, or cetyl alcohol. These compositions can be preserved by the addition of an anti-oxidant such as ascorbic acid. Dispersible powders and granules (suitable for preparation of an aqueous suspension by the addition of water) can contain the active ingredients in admixture with a dispersing agent, wetting agent, suspending agent, or combinations thereof. Additional excipients can also be present.

The pharmaceutical compositions of the invention can also be in the form of oil-in-water emulsions. The oily phase can be a vegetable oil, for example olive oil or arachis oil, or a mineral oil, for example liquid paraffin or mixtures of these. Suitable emulsifying agents can be naturally-occurring gums, such as gum acacia or gum tragacanth; naturally-occurring phospholipids, such as soy lecithin; esters or partial esters derived from fatty acids and hexitol anhydrides, such as sorbitan monooleate; and condensation products of said partial esters with ethylene oxide, such as polyoxyethylene sorbitan monooleate.

Transdermal delivery can be accomplished by means of iontophoretic patches and the like. The active ingredients can also be administered in the form of suppositories for rectal administration of the drug. These compositions can be prepared by mixing the active agents with a suitable non-irritating excipient which is solid at ordinary temperatures but liquid at the rectal temperature and will therefore melt in the rectum to release the drug. Such materials include cocoa butter and polyethylene glycols.

III. EXAMPLES

Example 1. Materials and Methods

Experimental design. Assays in cell culture were designed such that differences between control and experimental (i.e., knockout, dicer or siRNA-depleted, or drug-treated) groups could be compared using standard statistical tests described below and in the description of the drawings. All cell culture experiments were replicated at least three times independently. Animal experiments were performed using vehicle- or tamoxifen-treated mice and differences between groups compared statistically using methods described below.

Cell culture and generation of knockout and over-expression clones. WT cells were a HeLa cell line that stably over-expressed globotriaosylceramide, the cell surface receptor for STx1B and STx2B. This sub-line has been used for numerous assays on STx1 and STx2 over the last few years (8, 9). Culture conditions were identical to those described previously (8, 9). Mutations in genomic DNA were introduced using a lentivirus-based CRISPR/Cas9 system described by us recently (8). The guide RNA sequences were:

```
Rab2a:
                                    (SEQ ID NO: 9)
5'-CCA GTG CAT GAC CTT ACT AT-3';

ATG7:
                                    (SEQ ID NO: 10)
5'-GGT GAA CCT CAG TGA ATG TA-3';
and syntaxin17:
                                    (SEQ ID NO: 11)
5'-ATC AAA ATG CTG CAG AAT CG-3'.
```

Other procedures (production of lentivirus, infection of target cells with lentivirus, selection of single cell clones, and sequencing of genomic DNA) were conducted as previously described (8). To generate cells that over-expressed siRNA-resistant Vps39, WT cells were infected with lentivirus in which the transfer plasmid encoded Vps39 in a pLJM1 backbone vector (Addgene plasmid #34611, Cambridge, Mass.) using procedures identical to those previously described (8). The sequence of Vps39 in the transfer plasmid had 7 silent mutations in the region targeted by the siRNA (5'-CAA CCA TAT ATA ATC GCT-3')(SEQ ID NO: 12) so that the over-expressed construct was resistant to siRNA-mediated depletion.

Transient transfections using Dicer-Substrate Short Interfering RNAs (DsiRNAs), siRNA, and plasmid DNA. DsiRNAs targeting FUT1 or STAM and the control RNA, which did not target any human gene, were obtained from Integrated DNA Technologies (FUT1: hs.Ri.FUT1.13.3; STAM: hs.Ri.STAM.13.3; Control: #51-01-14-03). For transfections, cells were grown to ~40% confluency and transfected with 10 nM final concentration of each RNA duplex using Oligofectamine transfection reagent (Invitrogen) following manufacturer's instructions. Cultures were used for experiments 48 h after transfection.

Transfections with siRNAs were performed using Oligofectamine reagent essentially as described previously (8, 9). Sequences of GBF1 and control siRNAs were described previously (8, 38). Sequences of other siRNAs used were:

```
Vps39
sense:
                                   (SEQ ID NO: 13)
5'-gccucccuacaucauugcaTT-3', antisense:
                                   (SEQ ID NO: 14)
5'-ugcaaugauguagggaggcTG-3';

ATG7
sense:
                                   (SEQ ID NO: 15)
5'-gccagaggauucaacaugaTT-3', antisense:
                                   (SEQ ID NO: 16)
5'-ucauguugaauccucuggcTT-3';
and syntaxin17
sense:
                                   (SEQ ID NO: 17)
5'-ggaaaccuuagaagcggacuuaauu-3', antisense
                                   (SEQ ID NO: 18)
5'-aauuaaguccgcuucuaagguuucc-3'.
```

Except Vps39, experiments were performed 72 h post-transfection. To obtain robust Vps39 knockdown, it was necessary to transfect each culture with siRNA two-times. The second transfection was performed 48 h after the first, and cultures were analyzed 5 days after the first transfection. A similar protocol was used in prior studies to deplete Vps39 using siRNA (24).

Plasmid DNA was transfected using JetPEI reagent (VWR) as described previously (8, 9). Constructs encoding GFP-Rab5$_{WT}$, GFP-Rab7$_{WT}$, and GFP-Rab7$_{T22N}$ (dominant negative) have been previously described (8, 9). Plasmid encoding myc-tagged human Rab2a was from Addgene (plasmid #46779). Mutations were introduced into this plasmid using QuikChange (Agilent Technologies) (9).

PCR and RT-PCR. PCR and RT-PCR were performed as described previously (8). Primers used for RT-PCR were:

```
Rab2a FWD:
                               (SEQ ID NO: 19)
5'-cag aca aga ggt ttc agc cag tgc-3';

Rab2a REV:
                               (SEQ ID NO: 20)
5'-gct cct gct gca cct ctg taa tac-3';

FUT1 FWD:
                               (SEQ ID NO: 21)
5'-gcc ctg ctc aca cag tgc aac c-3';

FUT1 REV:
                               (SEQ ID NO: 22)
5'-ggc tta gcc aat gtc cca gag tgg-3';

STAM FWD:
                               (SEQ ID NO: 23)
5'-ctc tca gcc agg cag tgg tcc-3';

STAM REV:
                               (SEQ ID NO: 24)
5'-gca gta gcg gca gga gg-3';

ATG7 FWD:
                               (SEQ ID NO: 25)
5'-agt gac gat cgg atg aat ga-3';

ATG7 REV:
                               (SEQ ID NO: 26)
5'-tgg tct cat cgc tca tgt-3';

syntaxin17 FWD:
                               (SEQ ID NO: 27)
5'-tcg tgg gaa acct ta gaa gcgg-3';

syntaxin17 REV:
                               (SEQ ID NO: 28)
5'-gca gca ctg ttg aca tgg tct g-3';

Vps39 FWD:
                               (SEQ ID NO: 29)
5'-cct gaa ctg gac gga cat acc a-3';

Vps39 REV:
                               (SEQ ID NO: 30)
5'-ctt tgg acc aga agc ctc ggt t-3';

GAPDH FWD:
                               (SEQ ID NO: 31)
5'-ggc tac act gag cac cag gtg-3';

GAPDH REV:
                               (SEQ ID NO: 32)
5'-ggt cca ccc tgt tgc tg-3'.
```

Antibodies. Sources of antibodies used were as follows: Monoclonal anti-GM130 (#610822), anti-EEA1 (#610456), and anti-SNX1 (#611482) from BD Biosciences (San Jose, Calif.); monoclonal anti-Lamp2 (ab25631), and polyclonal anti-Vps26 (ab23892) from Abcam (Cambridge, UK); and polyclonal anti-LC3 A/B (D3U4C) from Cell Signaling Technologies (Danvers, Mass.). Polyclonal anti-giantin and anti-GRASP65 antibodies were described previously (8, 9).

STx1B and STx2B transport assays. Transport assays using fluorescently-labeled untagged STx1B or His-tagged STx2B were performed as previously described (8, 9). Briefly, cells were washed with ice-cold phosphate buffered saline (three times). After this, cells were incubated with 2 µg/mL of STx2B or 5 µg/ml of STx1B in transport media (Dulbecco's Modified Eagle Medium supplemented with 10% fetal bovine serum, 100 IU/mL penicillin-G and 100 µg/mL streptomycin) for 30 min on ice at 4° C. to allow toxin binding to the cell surface. Cells were then again washed with ice-cold phosphate buffered saline (three times) and transferred to toxin-free transport media at 37° C. to initiate toxin transport. Cultures were fixed after start of transport at times indicated in each figure and processed for microscopy.

Drug treatments in cell culture and viability assays. Tamoxifen (TAM), toremifene (TOR), raloxifene (RAL), bazedoxifene (BAZ), 4-hydroxytamoxifen (4HOT), endoxifen (END), ospemifene (OSP), bafilomycin A1 (BFA1), and chloroquine (CLQ) were purchased from Sigma-Aldrich (St. Louis, Mo.). Tamoxifen was used at 10 µM unless specified otherwise; toremifene, raloxifene, bazedoxifene, 4-hydroxytamoxifen, endoxifen, and ospemifene were used at 10 µM; bafilomycin A1 was used at 100 nM; and chloroquine was used at 50 µM. DMSO was added at 0.1% when used as a vehicle control. Leupeptin and pepstatin were used at final concentrations of 100 µg/ml and 50 µg/ml respectively, as described previously (8, 9). Compounds were present in the media during transport assays performed using STx1B or STx2B and during exposure to STx1 or STx2 holotoxins, which were obtained from BEI Resources (Manassas, VA). Cell viability was assessed using (3-(4,5-Dimethylthiazol-2-yl)-2,5-Diphenyltetrazolium Bromide 3-4-5 (MTT) reagent, as described recently (9).

Microscopy and image analyses. Immunofluorescence staining was performed as previously described (8, 9). For assessing pH of endolysosomal compartments, LysoSensor Green DND-189 probe (ThermoFisher, Waltham, MA) was used at 1 µM. Cells were exposed to the probe for 30 min and live cultures imaged immediately.

For imaging, a swept-field confocal microscope equipped with a four-line high-power laser launch and a 100×1.45 N.A. oil immersion objective (Nikon) was used. The camera was an iXon3 X3 DU897 electron-multiplying charge-coupled device camera (Andor Technology). All images were captured as z-stacks with 0.2-µm spacing between individual frames. Images depicted in the figures are maximum-intensity projections of the stacks.

All analyses were performed using ImageJ, available via the Internet from the National Institutes of Health. Particle counts were quantified using the Analyze Particles function; identical thresholds were used for control and experimental samples. Average fluorescence values per cell and Pearson's coefficient for colocalization were determined as described previously (8, 9). To quantify data obtained from the tandem mRFP-GFP-LC3 reporter, the percent of RFP-positive punctae that were also GFP-positive were quantified using the ComDet spots colocalization plugin. The Vps26 signal on EEA1-positive endosomes was measured as the percent of Vps26 signal in regions positive for EEA1 relative to the total cellular levels of Vps26 for each cell. EEA1 regions were identified for individual cells using the ComDet plugin. STx2B levels in the Golgi apparatus were quantified using the Golgi signal as the region of interest. To quantify perinuclear clustering of endosomal markers and lysosomes, the Radial Profile plugin was used on the average projection of acquired Z-stacks. Individual cells were outlined and isolated using the Clear Outside function. The center of mass of the measured signal was used as the radial center, and the distance distribution was measured over a 200 pixel (1250 µm) radius.

Mouse assays. All experiments with mice were approved by the Institutional Animal Care and Use Committee of UT Austin. Six-to-eight week old male Balb/c mice were used based on previous work (6) and pilot studies showing that these animals develop lethal toxicosis when injected with STx1 or STx2. Animals received one daily intraperitoneal injection of tamoxifen (70 mg tamoxifen/kg body weight) in 100 µL sunflower oil (tamoxifen group) or 100 µL sunflower oil (vehicle group) for five days. On the fifth day, animals received an additional intraperitoneal injection of STx1 (50 ng STx1/g body weight in 100 µL phosphate buffered saline) or STx2 (2.8 ng STx1/g body weight in 100 µL phosphate buffered saline). For animals that received oral tamoxifen after toxin injection, tamoxifen was provided in drinking water at an effective dose of 13 mg tamoxifen/kg body weight/day while vehicle-treated animals received drinking water without tamoxifen. After toxin injection, animals were monitored every 6 h for the onset of terminal morbidity at which point they were euthanized. Morbidly sick animals were positive for 3 of the following 5 signs: loss of >10% body weight, lethargy/decreased movement, dehydration, passage of loose stools, and onset of paralysis. Euthanasia was using carbon dioxide (39, 40).

Statistical analyses. All cell culture experiments were independently replicated at least three times. Student's t-test assuming equal variances was used to compare data between two groups. For comparisons between multiple groups, one-way ANOVA followed by Dunnett's or Tukey-Kramer post hoc test was used. Nonlinear regression was used to calculate the $LD_{50}$ of STx1 or STx2 in cell culture. Sample sizes for cell-based assays were based on power analyses and effect sizes, and designed to detect differences between groups at 80% power with p=0.05. Animal survival was assayed using the method of Kaplan Meier and the Gehan-Breslow-Wilcoxon and Log-rank (Mantel-Cox) tests. Mouse sample sizes were based on previous studies that utilized similar numbers of animals in STx1/STx2 survival assays (Mukhopadhyay and Lindstedt, supra; Tesh 1993). In all analyses, p<0.05 was considered statistically significant. Asterisks in graphs represent statistically significant differences.

Example 2. Biogenesis or Function of Lysosomes and/or Autophagy is Required for STx2 Transport and Toxicity To elucidate the mechanisms of STx2 trafficking, a viability-based genome-wide siRNA screen was recently performed, and 12 endosome/Golgi-localized host proteins were identified that, when depleted, reproducibly protected against STx2-induced cell death (8). Surprisingly, 6 of 12 identified hits (Rab2a, FUT1, STAM, TPCN1, SNX14 and VEGFR2) regulate lysosome biogenesis/function and/or autophagy (Table 1). Here, it was hypothesized that biogenesis or function of lysosomes and/or the autophagy pathway is required for the trafficking and toxicity of STx2, and targeting lysosomes/autophagy may provide a therapeutically-viable means to block STx2 trafficking.

TABLE 1

Role of TPCN1, Rab2a, SNX14, STAM, VEGFR2 and FUT1 in lysosome function and/or autophagy.

| Hit | Role in lysosome function/autophagy | Reference |
|---|---|---|
| TPCN1 | Endosome-localized calcium channel required for autophagy and lysosome maturation | (41) |
| Rab2a | Small GTPase historically associated with transport between the endoplasmic reticulum and the Golgi apparatus. Recent studies show that Rab2a also localizes to the endolysosomal system and is required for fusion of both late endosomes and autophagosomes with lysosomes. | (42-48) |
| SNX14 | Sorting nexin. Depletion leads to formation of enlarged lysosomes and accumulation of autophagosomes. | (49) |
| STAM | Part of the ESCRT-0 complex, which is required for the degradation of ubiquitylated proteins in lysosomes and formation of multivesicular endosomes. ESCRT-0 also plays a role in autophagy. | (50-53) |
| VEGFR2 | VEGFR2 signaling induces autophagy | (54) |
| FUT1 | Mediates fucosylation of the lysosomal membrane proteins Lamp1 and Lamp2. Depletion inhibits fucosylation of Lamp proteins, and alters autophagy and subcellular distribution of lysosomes. | (55) |

One hit, Rab2a, served as a first focus for testing this hypothesis, and a stable HeLa cell clone was generated in which Rab2a was depleted using a lentivirus-based CRISPR/Cas9 system. In the generated ΔRab2a clone, two separate stop codons were introduced in Rab2a, indicative of independent mutations in two chromosomes, and Rab2a transcript was not detectable (FIGS. 1A-B).

Lysosomes fuse with late endosomes or autophagosomes to degrade endocytic or autophagic cargo, respectively (14, 15). The cytosolic protein LC3 is recruited to autophagosomes and degraded after autophagosome-lysosome fusion (16). ΔRab2a cells had a higher number of LC3-positive punctae than wild-type (WT) cells (FIGS. 1C-D), indicating that autophagy and/or lysosome function was compromised. Toxin transport assays revealed that, consistent with prior studies (8, 9), in WT cells, STx2 B-subunit (STx2B) bound the cell surface and trafficked to the Golgi within 60 min (FIGS. 1E-F). In ΔRab2a cells, STx2B also bound the cell surface, but at 60 min, a pool of the toxin failed to traffic to the Golgi and instead was degraded (FIGS. 1E-F). At earlier time-points, in ΔRab2a cells, STx2B was detected in Rab5-positive punctae (FIG. 1G), indicating that internalization to early endosomes was not affected. Degradation of STx2B in ΔRab2a cells was blocked by pre-treatment with leupeptin/pepstatin or expression of dominant negative Rab7 (FIGS. 1H-J), indicating that the toxin was degraded in late endosomes/lysosomes. Toxin degradation in ΔRab2a cells, in spite of possible changes in lysosomal function, was not surprising because soluble cargo are effectively degraded in pre-lysosomal late endosomes, where proteolytic enzymes are active (17). The block in transport was rescued by over-expression of WT, but not dominant-negative or constitutively active, Rab2a (FIGS. 1K-L).

Identical results were obtained using a second clone in which the CRISPR/Cas9-system introduced a stop codon in one Rab2a allele and an inactivating point mutation in the other (data not shown). Moreover, dicer-mediated knockdown of two other hits, STAM or FUT1, enhanced LC3 punctae, blocked endosome-to-Golgi transport of STx2B, and induced STx2B degradation (data not shown). It was previously demonstrated that UNC50, another hit in the screen, mediated early endosome-to-Golgi transport of STx2B by recruiting the ARF-GEF GBF1 to Golgi membranes (8). Analyses of cells lacking UNC50 or depleted in GBF1 revealed enhanced LC3-positive punctae as well (data not shown). Thus, depletion of four separate proteins, Rab2a, STAM, FUT1 or UNC50, blocked trafficking of STx2B to the Golgi and also impacted lysosomes and/or autophagy, bolstering the hypothesis that formation/function of lysosomes and/or autophagy is itself required for toxin transport.

Example 3. Fusion of Late Endosomes with Lysosomes is Necessary for the Transport of STx2 From Early Endosomes to the Golgi, but the Autophagy Pathway is Dispensable To directly test the above hypothesis and distinguish between the role of lysosomes and autophagy, advantage was taken of the fact that the HOPS tethering complex is required for the fusion of both late endosomes and autophagosomes with lysosomes (18-20). Depletion of Vps39, a component of the HOPS complex, blocks both these membrane fusion events, and inhibits lysosome biogenesis/function as well as autophagy (18-20). In contrast, formation of autophagosomes requires ATG7 (21), and fusion of autophagosomes, but not late endosomes, with lysosomes requires syntaxin17 (20).

To test for the role of autophagy, ΔATG7 or Δsyntaxin17 cells were generated using CRISPR/Cas9. For both genes, the CRISPR/Cas9-system introduced stop codons in the genomic DNA and depleted transcript levels (FIGS. 2A-D). The mRFP-GFP-LC3 tandem reporter assay was used for autophagosome formation and autophagosome-lysosome fusion. The tandem reporter fluoresces in the red and green channels when recruited to autophagosomes, and only in the red channel after autophagosome-lysosome fusion due to quenching of GFP fluorescence (18, 20). In ΔATG7 cells, recruitment of the tandem reporter to punctate structures was inhibited under physiological or starvation conditions (data not shown), indicating that autophagosome formation was blocked. In Δsyntaxin17 cells, recruitment of the tandem reporter to punctate structures was not blocked, but the relative decrease in GFP-positive punctae observed in WT cells when autophagy was induced by starvation was not evident, indicating that the fusion of autophagosomes with lysosomes was inhibited. Consistent with a block in autophagosome-lysosome fusion in Δsyntaxin17 cells, levels of endogenous LC3 were also elevated. Notably, however, positioning of Lamp2-positive lysosomes, which is indicative of lysosomal dysfunction (22), was unaffected in Δsyntaxin17 or ΔATG7 cells. Thus, loss of ATG7 or syntaxin27 inhibited autophagy without affecting lysosomes. Importantly, transport of STx2B to the Golgi was not inhibited in ΔATG7 or Δsyntaxin17 cells (FIGS. 2E-J). Identical results were obtained when ATG7 or syntaxin17 was depleted using siRNA (FIGS. 2K-P). Overall, ATG7 and syntaxin17, and by extension autophagy, are not required for the early endosome-to-Golgi transport of STx2B.

Vps39 was subsequently depleted using siRNA since ΔVps39 cells could not be generated, likely because knockout of Vps39 is lethal (23). In knockdown cells, Vps39 transcript levels were depleted, endogenous LC3-positive punctae were enhanced, and Lamp2-positive lysosomes were clustered in the perinuclear area (FIGS. 3A-E), implying that lysosomal function and autophagy were compromised. In Vps39-depleted cells, STx2B was internalized into Rab5-positive early endosomes, but then failed to traffic to the Golgi, and instead was routed to Rab7-positive late endosomes and degraded (FIGS. 3F-I). The block in trafficking was rescued by expression of siRNA-resistant Vps39 (FIGS. 3J-L). The requirement of Vps39, but not ATG7 or syntaxin17, for STx2B trafficking implies that toxin transport depends on the function/biogenesis of lysosomes, but not the autophagy pathway.

Example 4. Inhibition of Late Endosome-Lysosome Fusion Alters Recruitment of Retromer to Early Endosomes By blocking late endosome-lysosome fusion, loss of Vps39 inhibits the protein degradation function of lysosomes as well as biogenesis of mature lysosomes (19). Treatment with lysosomal protease inhibitors did not block STx2B trafficking (FIGS. 3M-N), implying that toxin transport was independent of degradative function per se. Notably, in Vps39-depleted cells, endosomal maturation is also inhibited (24), likely due to defects in late endosome-lysosome fusion. Further, membrane recruitment of retromer, which is required for the early endosome-to-Golgi transport of STx2B (9), is linked to endosomal maturation (25). Thus, the block in late endosome-lysosome fusion in Vps39-depleted cells could indirectly inhibit early endosome-to-Golgi transport of STx2B by altering endosomal maturation and retromer function. Consistent with this, in Vps39 knockdown cells, EEA1- or SNX1-positive early endosomes were clustered in the perinuclear region, and association of the retromer component Vps26 with endosomal membranes was enhanced (FIGS. 3O-U). Since retromer function depends on its cyclic association with and dissociation from endosomal membranes, the increased association of Vps26 with early endosomes observed in Vps39-depleted cells may contribute to the block in STx2B transport. In totality, fusion of late endosomes, but not autophagosomes, with lysosomes is required for the early endosome-to-Golgi trafficking of STx2B, while function of lysosomes and the autophagy pathway is dispensable.

Example 5. Tamoxifen is a Potent Inhibitor of STx1 and STx2 Transport and Toxicity It is challenging to bring a new small molecule into therapeutic use, and an alternative approach of repurposing a drug approved for treatment of another disease was pursued here. Small molecules that increase the pH of the endolysosomal compartment inhibit fusion of late endosomes with lysosomes (26, 27), block early endosome-to-Golgi protein transport (28), and protect against STx1-induced cytotoxicity (29). Notably, previous studies by the present inventors have indicated that there are critical differences in the molecular factors required for the trafficking of STx1 and STx2 (7,8). Therefore, it could not be predicted whether alterations of endolysosomal pH could effectively inhibit trafficking and toxicity of STx2. As described below, experiments were conducted to test whether drugs currently approved by the FDA that alter pH of the endolysosomal compartment could be repurposed as a STx2-transport inhibitor. Results summarized in FIG. 4 validated that treatment with the V-ATPase inhibitor bafilomycin A1 robustly inhibited the transport of STx2B to the Golgi apparatus (FIGS. 4A-B). A subsequent screen of FDA-approved lysosome-targeting drugs identified two compounds that increase endolysosomal pH, tamoxifen and chloroquine, to be inhibitors of STx2B transport (FIGS. 4A-B). Chloroquine and tamoxifen are lysosomotropic weak bases that accumulate within lysosomes/acidic compartments and directly increase pH (26, 30-32) (see below). Subsequent studies focused on tamoxifen, which had a greater inhibitory effect and is currently approved for breast cancer therapy (33, 34).

Similar to Vps39-depleted cells, in tamoxifen-treated cells, LC3-positive punctae were elevated, and while STx2B bound the cell surface and reached Rab5-positive early endosomes, the toxin failed to traffic to the Golgi and instead was rerouted to Rab7-positive late endosomes and degraded (FIGS. 4A-D). Tamoxifen also inhibited the transport of STx1 B-subunit (STx1B) to the Golgi and induced degradation of STx1B (FIGS. 4E-F).

Example 6. Tamoxifen Protects Cells Against STx1 and STx2 Toxicity by Acting as a Weak Base that Directly Increases Endolysosomal pH Subsequent experiments were made to determine whether tamoxifen could protect cells against STx1- or STx2-induced death and elucidate its mechanism of action. Treatment with 10 tamoxifen provided ~200-fold protection against STx2-induced cell death and ~50-fold protection against STx1 without inducing cytotoxicity (FIG. 5A). Protection was evident at tamoxifen doses as low as 2.5 µM (FIG. 5B).

The protective effect of tamoxifen was related to its capability to increase endolysosomal pH. Presence of a tertiary amine makes tamoxifen a weak base (FIG. 5C) (31). Prior studies indicate that this weak base property allows tamoxifen to directly titrate the pH of endolysosomal compartments upwards (i.e. increase endolysosomal pH), and that tamoxifen-mediated changes in endolysosomal pH are independent of estrogen receptors or any cellular protein (30, 31). HeLa cells do not express estrogen receptors (35), ruling out a role for estrogen signaling in the assays used herein. If the protective effect of tamoxifen was based on an increase in endolysosomal pH, tamoxifen derivatives or metabolites that lack the tertiary amine and cannot function as a weak base should not protect against STx2 toxicity. Indeed, three clinically-approved compounds with the tertiary amine, toremifene, raloxifene, and bazedoxifene, provided as much protection as tamoxifen against STx2-induced cell death (FIGS. 5C-E). Toremifene and raloxifene did not alter cell viability by themselves, but bazedoxifene had noticeable cytotoxicity at concentrations used (FIG. 5D). A lower level of protection was evident with the metabolite 4-hydroxytamoxifen, which also has the tertiary amine (FIGS. 5C-E); the reduced protective effect was likely due to the presence of the aliphatic hydroxyl group that may inhibit membrane incorporation. In contrast, protection provided by the metabolite endoxifen, which has a secondary amine and is a weaker base than the tertiary amine-containing compounds, was substantially weaker than tamoxifen or 4-hydroxytamoxifen (FIGS. 5C-E). Furthermore, the compound ospemifene, which does not have an amine group and is not a weak base, failed to protect all together (FIGS. 5C-E). It was verified that toremefine blocked transport of STx2B to the Golgi, but ospemifene did not (data not shown). Thus, the tertiary amine group of tamoxifen is necessary to protect against toxin-induced cell death, implying that protection is provided by the weak base effect of tamoxifen.

To directly determine the mechanism by which increased endolysosomal pH impacted toxin transport and toxicity, time-course assays were performed. A 24 h pre-treatment with tamoxifen or bafilomycin A1 was necessary to block STx2B transport, and treatment for shorter durations (e.g., 4 h), did not have an effect (FIGS. 5F-G and FIGS. 4A-B). However, similar to several lysoso, motropic compounds, tamoxifen induces a transient change in endolysosomal pH with an increase evident at early time-points (30-60 min) but not 24 h after treatment (32). These results were verified for tamoxifen and a similar effect was observed for bafilomycin A1 (FIGS. 5H-I). A possibility is that a change in endolysosomal pH initiates a cascade of events that leads to a block in transport at a later time point. Consistent with this, morphological differences were apparent in the endolysosomal compartments of cells treated with tamoxifen or bafilomycin A for 24 h (FIG. 5H). Furthermore, and similar to results obtained with Vps39-depletion, 24 h, but not 30 min, after tamoxifen treatment, positioning of early endosomes gained a perinuclear prominence and recruitment of the retromer component Vps26 to early endosomes was enhanced (FIGS. 5J-L). Additionally, toremefine, which has the tertiary amine group, increased endolysosomal pH at 30 min and increased Vps26 levels on early endosomes at 24 h, while ospemifene, which lacks the tertiary amine, did not (data not shown). Overall, the results indicate that tamoxifen phenocopies Vps39-depletion with regards to protein transport at the early endosome/Golgi interface and inhibits transport and toxicity of STx1 and STx2.

Example 7. Tamoxifen Protects Mice Against Lethal STx1 or STx2 Toxicosis

To test the disease relevance of these results, experiments were performed at the whole-organism level using a mouse model in which animals were given a single intraperitoneal injection of STx1 or STx2. This model produces fulminant toxicosis and the observed renal damage has similarities with changes seen in human patients (6, 12, 36). Animals were pre-treated with 70 mg tamoxifen/kg body weight or vehicle for 5 days before toxin exposure. The pre-treatment regimen was utilized because, in humans, the toxins enter the bloodstream ~10-14 days after bacterial infection and ~4-7 days after development of symptomatic diarrhea (2, 3), providing a window of opportunity for diagnosis and initiation of anti-toxin therapy. Additionally, mice are more efficient at handling tamoxifen than humans, and the regimen was designed to produce serum levels similar to humans receiving tamoxifen at the currently approved dose of 20 mg/day (33, 34). Vehicle-treated mice exposed to 50 ng STx1/g body weight died within 3-4 days (FIG. 5M). As expected, STx2 was more toxic, and vehicle-treated mice exposed to 2.8 ng STx2/g body weight died within 2-3 days (FIG. 5M). Importantly, tamoxifen treatment significantly improved the survival of STx1- or STx2-treated mice (FIG. 5M). In the STx1-group, a subset of tamoxifen-treated mice remained healthy until the end of the experiment (FIG. 5M). Tamoxifen-treated mice that received STx2 also survived for significantly longer than those that received vehicle (FIG. 5M). A similar level of protection against STx2 was evident when, in addition to the pre-treatment, tamoxifen was also orally delivered via drinking water after STx2-injection (FIG. 5M).

IV. REFERENCES

1. Mead P S, et al. (1999) Food-related illness and death in the United States. *Emerg Infect Dis* 5(5):607-625.
2. Nataro J P P L (2006) *Oski's Paediatrics: Principles and Practice*, ed McMillan J A F R, DeAngelis C D, Douglas Jones, M Jr. (Lippincott Williams and Wilkins, Philadelphia), pp 1063-1068.
3. Obrig T G (2010) *Escherichia coli* Shiga Toxin Mechanisms of Action in Renal Disease. *Toxins (Basel)* 2(12):2769-2794.

4. Beddoe T, Paton A W, Le Nours J, Rossjohn J, & Paton J C (2010) Structure, biological functions and applications of the AB5 toxins. *Trends Biochem Sci* 35(7):411-418.
5. Mukhopadhyay S & Linstedt A D (2013) Retrograde trafficking of AB(5) toxins: mechanisms to therapeutics. *J Mol Med (Berl)* 91(10):1131-1141.
6. Mukhopadhyay S & Linstedt A D (2012) Manganese blocks intracellular trafficking of Shiga toxin and protects against Shiga toxicosis. *Science* 335(6066):332-335.
7. Mukhopadhyay S, Redler B, & Linstedt A D (2013) Shiga toxin-binding site for host cell receptor GPP130 reveals unexpected divergence in toxin-trafficking mechanisms. *Mol Biol Cell* 24(15):2311-2318.
8. Selyunin A S, Iles L R, Bartholomeusz G, & Mukhopadhyay S (2017) Genome-wide siRNA screen identifies UNC50 as a regulator of Shiga toxin 2 trafficking. *J Cell Biol* 216(10):3249-3262.
9. Selyunin A S & Mukhopadhyay S (2015) A Conserved Structural Motif Mediates Retrograde Trafficking of Shiga Toxin Types 1 and 2. *Traffic* 16(12):1270-1287.
10. Saenz J B, Doggett T A, & Haslam D B (2007) Identification and characterization of small molecules that inhibit intracellular toxin transport. *Infect Immun* 75(9):4552-4561.
11. Stechmann B, et al. (2010) Inhibition of retrograde transport protects mice from lethal ricin challenge. *Cell* 141(2):231-242.
12. Tesh V L, et al. (1993) Comparison of the relative toxicities of Shiga-like toxins type I and type II for mice. *Infect Immun* 61(8):3392-3402.
13. Boerlin P, et al. (1999) Associations between virulence factors of Shiga toxin-producing *Escherichia coli* and disease in humans. *J Clin Microbiol* 37(3):497-503.
14. Luzio J P, Hackmann Y, Dieckmann N M, & Griffiths G M (2014) The biogenesis of lysosomes and lysosome-related organelles. *Cold Spring Harb Perspect Biol* 6(9):a016840.
15. Shen H M & Mizushima N (2014) At the end of the autophagic road: an emerging understanding of lysosomal functions in autophagy. *Trends Biochem Sci* 39(2):61-71.
16. Tanida I, Ueno T, & Kominami E (2008) LC3 and Autophagy. *Methods Mol Biol* 445:77-88.
17. Tjelle T E, Brech A, Juvet L K, Griffiths G, & Berg T (1996) Isolation and characterization of early endosomes, late endosomes and terminal lysosomes: their role in protein degradation. *J Cell Sci* 109 (Pt 12):2905-2914.
18. Wartosch L, Gunesdogan U, Graham S C, & Luzio J P (2015) Recruitment of VPS33A to HOPS by VPS16 Is Required for Lysosome Fusion with Endosomes and Autophagosomes. *Traffic* 16(7):727-742.
19. Pols M S, ten Brink C, Gosavi P, Oorschot V, & Klumperman J (2013) The HOPS proteins hVps41 and hVps39 are required for homotypic and heterotypic late endosome fusion. *Traffic* 14(2):219-232.
20. Jiang P, et al. (2014) The HOPS complex mediates autophagosome-lysosome fusion through interaction with syntaxin 17. *Mol Biol Cell* 25(8):1327-1337.
21. Komatsu M, et al. (2005) Impairment of starvation-induced and constitutive autophagy in Atg7-deficient mice. *J Cell Biol* 169(3):425-434.
22. Willett R, et al. (2017) TFEB regulates lysosomal positioning by modulating TMEM55B expression and JIP4 recruitment to lysosomes. *Nat Commun* 8(1):1580.
23. Messler S, et al. (2011) The TGF-beta signaling modulators TRAP1/TGFBRAP1 and VPS39/Vam6/TLP are essential for early embryonic development. *Immunobiology* 216(3):343-350.
24. Rink J, Ghigo E, Kalaidzidis Y, & Zerial M (2005) Rab conversion as a mechanism of progression from early to late endosomes. *Cell* 122(5):735-749.
25. Burd C & Cullen P J (2014) Retromer: a master conductor of endosome sorting. *Cold Spring Harb Perspect Biol* 6(2).
26. Huotari J & Helenius A (2011) Endosome maturation. *EMBO J* 30(17):3481-3500.
27. van Weert A W, Dunn K W, Geuze H J, Maxfield F R, & Stoorvogel W (1995) Transport from late endosomes to lysosomes, but not sorting of integral membrane proteins in endosomes, depends on the vacuolar proton pump. *J Cell Biol* 130(4):821-834.
28. Chapman R E & Munro S (1994) Retrieval of TGN proteins from the cell surface requires endosomal acidification. *EMBO J* 13(10):2305-2312.
29. Dyve Lingelem A B, Bergan J, & Sandvig K (2012) Inhibitors of intravesicular acidification protect against Shiga toxin in a pH-independent manner. *Traffic* 13(3):443-454.
30. Altan N, Chen Y, Schindler M, & Simon S M (1999) Tamoxifen inhibits acidification in cells independent of the estrogen receptor. *Proc Natl Acad Sci USA* 96(8):4432-4437.
31. Chen Y, Schindler M, & Simon S M (1999) A mechanism for tamoxifen-mediated inhibition of acidification. *J Biol Chem* 274(26):18364-18373.
32. Lu S, Sung T, Lin N, Abraham R T, & Jessen B A (2017) Lysosomal adaptation: How cells respond to lysosomotropic compounds. *PLoS One* 12(3):e0173771.
33. Lazzeroni M, et al. (2012) Oral low dose and topical tamoxifen for breast cancer prevention: modern approaches for an old drug. *Breast Cancer Res* 14(5):214.
34. Robinson S P, Langan-Fahey S M, Johnson D A, & Jordan V C (1991) Metabolites, pharmacodynamics, and pharmacokinetics of tamoxifen in rats and mice compared to the breast cancer patient. *Drug Metab Dispos* 19(1):36-43.
35. Touitou I, Mathieu M, & Rochefort H (1990) Stable transfection of the estrogen receptor cDNA into Hela cells induces estrogen responsiveness of endogenous cathepsin D gene but not of cell growth. *Biochem Biophys Res Commun* 169(1):109-115.
36. Mohawk K L & O'Brien A D (2011) Mouse models of *Escherichia coli* O157:H7 infection and shiga toxin injection. *J Biomed Biotechnol* 2011:258185.
37. Saftig P & Klumperman J (2009) Lysosome biogenesis and lysosomal membrane proteins: trafficking meets function. *Nat Rev Mol Cell Biol* 10(9):623-635.
38. Leyva-Illades D, et al. (2014) SLC30A10 Is a Cell Surface-Localized Manganese Efflux Transporter, and Parkinsonism-Causing Mutations Block Its Intracellular Trafficking and Efflux Activity. *J Neurosci* 34(42):14079-14095.
39. Liu C, et al. (2017) Hypothyroidism induced by loss of the manganese efflux transporter SLC30A10 may be explained by reduced thyroxine production. *J Biol Chem* 292(40):16605-16615.
40. Hutchens S, et al. (2017) Deficiency in the manganese efflux transporter SLC30A10 induces severe hypothyroidism in mice. *J Biol Chem* 292(23):9760-9773.

41. Garcia-Rua V, et al. (2016) Endolysosomal two-pore channels regulate autophagy in cardiomyocytes. *J Physiol* 594(11):3061-3077.
42. Tisdale E J (2000) Rab2 requires PKC iota/lambda to recruit beta-COP for vesicle formation. *Traffic* 1(9):702-712.
43. Tisdale E J & Balch W E (1996) Rab2 is essential for the maturation of pre-Golgi intermediates. *J Biol Chem* 271(46):29372-29379.
44. Tisdale E J, Bourne J R, Khosravi-Far R, Der C J, & Balch W E (1992) GTP-binding mutants of rab1 and rab2 are potent inhibitors of vesicular transport from the endoplasmic reticulum to the Golgi complex. *J Cell Biol* 119(4):749-761.
45. Tisdale E J & Jackson M R (1998) Rab2 protein enhances coatomer recruitment to pre-Golgi intermediates. *J Biol Chem* 273(27):17269-17277.
46. Fujita N, et al. (2017) Genetic screen in Drosophila muscle identifies autophagy-mediated T-tubule remodeling and a Rab2 role in autophagy. *Elife* 6.
47. Gillingham A K, Sinka R, Tones I L, Lilley K S, & Munro S (2014) Toward a comprehensive map of the effectors of rab GTPases. *Dev Cell* 31(3):358-373.
48. Lorincz P, et al. (2017) Rab2 promotes autophagic and endocytic lysosomal degradation. *J Cell Biol* 216(7):1937-1947.
49. Akizu N, et al. (2015) Biallelic mutations in SNX14 cause a syndromic form of cerebellar atrophy and lysosome-autophagosome dysfunction. *Nat Genet* 47(5):528-534.
50. Bache K G, Raiborg C, Mehlum A, & Stenmark H (2003) STAM and Hrs are subunits of a multivalent ubiquitin-binding complex on early endosomes. *J Biol Chem* 278(14):12513-12521.
51. Lloyd T E, et al. (2002) Hrs regulates endosome membrane invagination and tyrosine kinase receptor signaling in Drosophila. *Cell* 108(2):261-269.
52. Ren X, et al. (2009) Hybrid structural model of the complete human ESCRT-0 complex. *Structure* 17(3):406-416.
53. Rusten T E & Stenmark H (2009) How do ESCRT proteins control autophagy? *J Cell Sci* 122(Pt 13):2179-2183.
54. Poluzzi C, et al. (2014) Endorepellin evokes autophagy in endothelial cells. *J Biol Chem* 289(23):16114-16128.
55. Tan K P, et al. (2016) Fucosylation of LAMP-1 and LAMP-2 by FUT1 correlates with lysosomal positioning and autophagic flux of breast cancer cells. *Cell Death Dis* 7(8):e2347.

Although the foregoing invention has been described in some detail by way of illustration and example for purposes of clarity and understanding, one of skill in the art will appreciate that certain changes and modifications may be practiced with the scope of the appended claims. In addition, each reference provided herein is incorporated by reference in its entirety to the same extent as if each reference was individually incorporated by reference.

What is claimed is:

1. A method for treating Shiga toxicosis, the method comprising administering to a subject in need thereof an effective amount of an active agent selected from the group consisting of tamoxifen, 4-hydroxytamoxifen, endoxifen, toremifene, raloxifene, bazedoxifene, and pharmaceutically acceptable salts thereof.

2. The method of claim 1, wherein the active agent is selected from the group consisting of tamoxifen, toremifene, raloxifene, and pharmaceutically acceptable salts thereof.

3. The method of claim 1, wherein the subject is infected with a Shiga toxin-producing *Escherichia* species, a Shiga toxin-producing *Shigella* species, or a combination thereof.

4. The method of claim 3, wherein the subject is infected with Shiga toxin-producing *E. coli*.

5. The method of claim 1, wherein the active agent is administered to the subject within ten days of the infection.

6. The method of claim 1, wherein the subject exhibits symptomatic diarrhea.

7. The method of claim 6, wherein the active agent is administered to the subject within three days of the onset of symptomatic diarrhea.

8. The method of claim 1, wherein the active agent is administered in an amount ranging from about 0.1 mg/kg/day to about 100 mg/kg/day.

9. The method of claim 8, wherein the active agent is administered in an amount ranging from about 0.1 mg/kg/day to about 1.0 mg/kg/day.

10. The method of claim 1, wherein the active agent is administered orally.

11. The method of claim 1, further comprising administering an antibiotic to the subject.

12. The method of claim 1, further comprising administering a manganese compound to the subject.

* * * * *